(12) United States Patent
Aissaoui et al.

(10) Patent No.: US 8,288,411 B2
(45) Date of Patent: Oct. 16, 2012

(54) PYRROLIDINES AND PIPERIDINES AS OREXIN RECEPTOR ANTAGONISTS

(75) Inventors: Hamed Aissaoui, Pulversheim (FR); Christoph Boss, Allschwil (CH); Ralf Koberstein, Lorrach (GE); Thierry Sifferlen, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 222 days.

(21) Appl. No.: 12/679,535

(22) PCT Filed: Sep. 23, 2008

(86) PCT No.: PCT/IB2008/053861
§ 371 (c)(1),
(2), (4) Date: Mar. 23, 2010

(87) PCT Pub. No.: WO2009/040730
PCT Pub. Date: Apr. 2, 2009

(65) Prior Publication Data
US 2010/0197733 A1 Aug. 5, 2010

(30) Foreign Application Priority Data
Sep. 24, 2007 (WO) .................. PCT/IB2007/053863

(51) Int. Cl.
*A61K 31/454* (2006.01)
*C07D 401/14* (2006.01)
(52) U.S. Cl. .................. 514/318; 546/193; 546/194
(58) Field of Classification Search .................. 514/318; 546/193, 194
See application file for complete search history.

(56) References Cited

U.S. PATENT DOCUMENTS

| | | | |
|---|---|---|---|
| 6,943,160 B2 | 9/2005 | Branch et al. | |
| 7,166,608 B2 | 1/2007 | Branch et al. | |
| 7,365,077 B2 | 4/2008 | Branch et al. | |
| 7,423,052 B2 | 9/2008 | Chan et al. | |
| 7,432,270 B2 | 10/2008 | Branch et al. | |
| 7,470,710 B2 | 12/2008 | Branch et al. | |
| 7,582,661 B2 * | 9/2009 | Ugashe et al. | 514/354 |
| 7,897,627 B2 | 3/2011 | Knust et al. | |
| 7,994,336 B2 | 8/2011 | Aissaoui et al. | |
| 8,030,495 B2 | 10/2011 | Coleman et al. | |
| 2003/0186964 A1 | 10/2003 | Branch et al. | |
| 2004/0192673 A1 | 9/2004 | Gaillard et al. | |
| 2006/0014733 A1 | 1/2006 | Howard et al. | |
| 2006/0040937 A1 | 2/2006 | Branch et al. | |
| 2009/0022670 A1 | 1/2009 | Alvaro et al. | |
| 2010/0016401 A1 | 1/2010 | Aissaoui et al. | |
| 2010/0069418 A1 | 3/2010 | Aissaoui et al. | |
| 2010/0113531 A1 | 5/2010 | Aissaoui et al. | |
| 2010/0168134 A1 | 7/2010 | Breslin et al. | |
| 2010/0184808 A1 | 7/2010 | Aissaoui et al. | |
| 2010/0204285 A1 | 8/2010 | Aissaoui et al. | |
| 2010/0210667 A1 | 8/2010 | Alvaro et al. | |
| 2010/0222328 A1 | 9/2010 | Aissaoui et al. | |
| 2011/0009401 A1 | 1/2011 | Aissaoui et al. | |
| 2011/0009461 A1 | 1/2011 | Aissaoui et al. | |
| 2011/0039857 A1 | 2/2011 | Aissaoui et al. | |
| 2011/0124636 A1 | 5/2011 | Aissaoui et al. | |

FOREIGN PATENT DOCUMENTS

| | | |
|---|---|---|
| WO | WO 01/96302 | 12/2001 |
| WO | WO 02/44172 | 6/2002 |
| WO | WO 03/041711 | 5/2003 |
| WO | WO 03/051368 | 6/2003 |
| WO | WO 03/051873 | 6/2003 |
| WO | WO 2004/041791 | 5/2004 |
| WO | WO 2004/041807 | 5/2004 |
| WO | WO 2004/041816 | 5/2004 |
| WO | WO 2009/143033 | 11/2009 |

OTHER PUBLICATIONS

Coleman et al. "Oresin receptor antagonists . . . " Exp. Opin. Ther Patent 20(3)307-324 (2010).*
Chemelli, R.M., et al., "Narcolepsy in Orexin Knockout Mice: Molecular Genetics of Sleep Regulation", Cell, vol. 98, pp. 437-451, (1999).
Gould, P.L., "Salt Selection for Basic Drugs", International Journal of Pharmaceutics, vol. 33, pp. 201-217, (1986).
March, J. et al., "Advanced Organic Chemistry", 4th Edition, John Wiley & Sons, pp. 447-449, 919-920, and 1167-1171, (1986).
Remington, The Science and Practice of Pharmacy, 21st Edition (2005), Part 5, "Pharmaceutical Manufacturing" [published by Lippincott Williams & Wilkins].
Sakurai, T., et al., "Orexins and Orexin Receptors: A Family of Hypothalamic Neuropeptides and G Protein-Coupled Receptors that Regulate Feeding Behavior", Cell, vol. 92, pp. 573-585, (1998).
Aissaoui et al; "N-Glycine-Sulfonamides as Potent Dual Orexin 1/Orexin 2 Receptor Antagonists"; Bioorganic & Medicinal Chemistry Letters, vol. 18, pp. 5729-5733, 2008.
Bergman, Bioorganic & Medicinal Chemistry Letters, 2008, vol. 18, 1425-1430.
Bohm et al, "Scaffold Hopping"; Drug Disc. Today Tech, 2004, vol. 1, issue 3, pp. 217-224.

(Continued)

*Primary Examiner* — Celia Chang
(74) *Attorney, Agent, or Firm* — Hoxie & Associates LLC

(57) ABSTRACT

The invention relates to compounds of formula (I) wherein Y, A, N and $R^1$ are as described in the description, to salts, especially pharmaceutically acceptable salts, of such compounds and to the use of such compounds as medicaments, especially as orexin receptor antagonists.

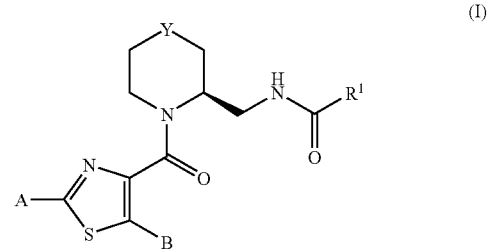

11 Claims, No Drawings

OTHER PUBLICATIONS

Boss et al; "Biomedical Application of Orexin/Hypocretin Receptor Ligands in Neuroscience"; Journal of Medicinal Chemistry, Vo;1. 52, No. 4, pp. 891-903; 2009.

Boss et al; "Orexin Receptor Antagonism: A New Principle in Neuroscience"; CHIMIA; vol. 62, No. 12, pp. 974-979, 2008.

Cai et al; "Antagonists of the Orexin Receptors, Expert Opinion on Therapeutic Patents", Inform Healthcare, GB, vol. 16, No. 5, pp. 631-646, May 1, 2006.

Cox, Bioorganic & Medicinal Chemistry Letter, 2009, vol. 19, 2997-3001.

Gatfield et al; "Orexin Receptor Antagonists: A New Concept in CNS Disorders"; ChemMedChem, vol. 5, pp. 1197-1214, 2010.

Langmead et al; "Characterisation of the Binding of [3H]-SB-674042, a Novel Nonpeptide Antagonist, to the Human Orexin-1 Receptor"; British Journal of Pharmacology, vol. 141, pp. 340-346, 2004.

Roecker, Current Topic Medicinal Chemistry, 2008, vol. 8, 977-987.

Sifferlen et al; "Novel Pyrazolo-Tetrahydropyridines as Potent Orexin Receptor Antagonists"; Bioorganic & Medicinal Chemistry Letters, vol. 20, pp. 1539-1542, 2010.

* cited by examiner

PYRROLIDINES AND PIPERIDINES AS OREXIN RECEPTOR ANTAGONISTS

CROSS REFERENCE TO RELATED APPLICATIONS

This application is a United States Application under 35 U.S.C. 371 claiming benefit of PCT Application No. PCT/IB2008/053861, filed on Sep. 23, 2008, which claims the benefit of PCT Application No. PCT/IB2007/053863, filed on Sep. 24, 2007 the contents of each of which are incorporated herein by reference.

The present invention relates to novel pyrrolidine- and piperidine-derivatives of formula I and their use as pharmaceuticals. The invention also concerns related aspects including processes for the preparation of the compounds, pharmaceutical compositions containing one or more compounds of formula I, and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., *Cell* (1998), 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell (1998), 92, 573-585). On the other hand, it was also observed that orexins regulate states of sleep and wakefulness opening potentially novel therapeutic approaches to narcolepsy as well as insomnia and other sleep disorders (Chemelli R. M. et al., *Cell* (1999), 98, 437-451).

Orexin receptors are found in the mammalian brain and may have numerous implications in pathologies as known from the literature.

The present invention provides pyrrolidine- and piperidine-derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO 01/96302.

The present invention describes novel pyrrolidine- and piperidine-derivatives as orexin receptor antagonists.

Various embodiments of the invention are presented hereafter:

i) The invention firstly relates to compounds of formula I

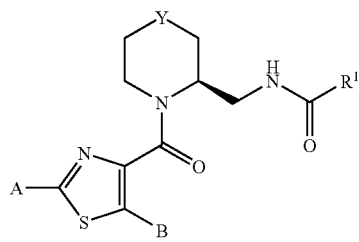

I wherein

Y represents $(CH_2)_n$, wherein n represents 0 or 1;
A represents pyridyl, unsubstituted phenyl or phenyl mono- or di-substituted with substituents independently selected from the group consisting of $(C_{1-4})$alkyl, $(C_{1-4})$alkoxy, trifluoromethyl and halogen;
B represents phenyl which is unsubstituted or mono- or di-substituted with substituents independently selected from the group consisting of $(C_{1-4})$alkyl, $(C_{1-4})$alkoxy, trifluoromethyl and halogen; and
$R^1$ represents aryl or heterocyclyl, wherein the aryl or heterocyclyl is unsubstituted or mono-, di-, or tri-substituted with substituents independently selected from the group consisting of $(C_{1-4})$alkyl, $(C_{1-4})$alkoxy, halogen and trifluoromethyl, or $R^1$ represents one of the 2,3-dihydro-benzofuranyl, benzo[1,3]dioxolyl, 2,3-dihydro-benzo[1,4]dioxinyl and 4H-benzo[1,3]dioxinyl groups, which groups are unsubstituted or mono- or di-substituted with substituents independently selected from the group consisting of $(C_{1-4})$alkyl, $(C_{1-4})$alkoxy and halogen;
and to salts (in particular pharmaceutically acceptable salts) of compounds of formula I.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art. For avoidance of any doubt, the chiral carbon atom of the piperidine- or pyrrolidine moiety of the compounds of formula I or the compounds of formula $I_{CE}$ below is in absolute (S)-configuration.

The general terms used hereinbefore and hereinafter preferably have, within this disclosure, the following meanings, unless otherwise indicated:

The term "halogen" means fluorine, chlorine, or bromine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, n-propyl, iso-propyl, n-butyl, iso-butyl, sec-butyl and tent-butyl. Preferred are methyl and ethyl (and notably methyl).

The term "$(C_{1-4})$alkoxy", alone or in combination, means a group of the formula $(C_{1-4})$alkyl-O— in which the term "$(C_{1-4})$alkyl" has the previously given significance, such as methoxy, ethoxy, n-propoxy, iso-propoxy, n-butoxy, iso-butoxy, sec-butoxy and tert-butoxy. Preferred are methoxy and ethoxy. More preferred is methoxy.

The term "aryl", alone or in combination, means a phenyl or a naphthyl group. Preferred is a phenyl group. The aryl group may be unsubstituted or mono-, di-, or tri-substituted wherein the substituents are independently selected from the group consisting of $(C_{1-4})$alkyl, $(C_{1-4})$alkoxy, trifluoromethyl and halogen.

The term "heterocyclyl", alone or in combination, means a 5- to 10-membered monocyclic or bicyclic aromatic ring containing 1, 2 or 3 heteroatoms independently selected from oxygen, nitrogen and sulfur. Examples of such heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl and imidazo[2,1-b]thiazolyl. The above-mentioned heterocyclyl groups may also be mono-, di-, or tri-substituted wherein the substituents are independently selected from the group consisting of $(C_{1-4})$alkyl, $(C_{1-4})$alkoxy, halogen and trifluoromethyl.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, a dashed line in a partial structure drawing shows the point where the drawn radical is attached to the rest of the molecule.

ii) In particular, the invention relates to compounds of formula I that are also compounds of formula $I_{CE}$

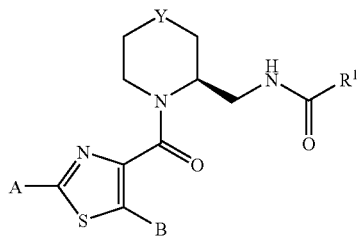

$I_{CE}$ wherein

Y represents $(CH_2)_n$, wherein n represents 0 or 1;

A represents pyridyl, unsubstituted phenyl or phenyl which is mono- or di-substituted with substituents independently selected from the group consisting of $(C_{1-4})$alkyl, $(C_{1-4})$alkoxy, trifluoromethyl and halogen (and preferably independently selected from the group consisting of $(C_{1-4})$alkyl, $(C_{1-4})$alkoxy and halogen);

B represents phenyl which is unsubstituted or substituted once with $(C_{1-4})$alkyl, $(C_{1-4})$alkoxy, trifluoromethyl or halogen (and preferably with $(C_{1-4})$alkyl, trifluoromethyl or halogen); and $R^1$ represents an 8-membered bicyclic aromatic ring containing 1, 2 or 3 heteroatoms independently selected from oxygen, nitrogen and sulphur, which aromatic ring may be substituted once by $(C_{1-4})$alkyl (said 8- to 10-membered bicyclic aromatic ring being in particular imidazo[2,1-b]thiazol-5-yl and $R^1$ being in particular 6-methyl-imidazo[2,1-b]thiazol-5-yl), or $R^1$ represents a 2,3-dihydrobenzofuran-4-yl, 1H-indol-3-yl or 1H-indazol-3-yl group which may be substituted once with $(C_{1-4})$alkyl (in particular by methyl);

and to salts (in particular pharmaceutically acceptable salts) of compounds of formula $I_{CE}$.

iii) According to a preferred embodiment of this invention, the compounds of formula I as defined in embodiment i) or ii) above or their salts (among which the pharmaceutically acceptable salts will be preferred) wherein $R^1$ is heterocyclyl will be such that $R^1$ is one of the following groups:

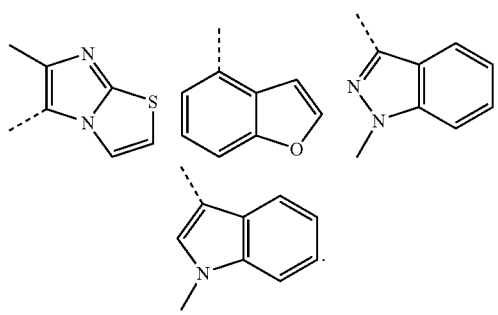

iv) Another preferred embodiment of this invention relates to the compounds of formula I as defined in embodiment i), ii) or iii) above or their salts (among which the pharmaceutically acceptable salts will be preferred) wherein, when $R^1$ is different from aryl and heterocyclyl, $R^1$ represents

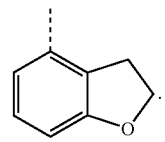

v) A further embodiment of the invention relates to compounds of formula I as defined in one of embodiments i) to iv) or their salts (among which the pharmaceutically acceptable salts will be preferred), wherein B represents phenyl which is unsubstituted or mono- or di-substituted with substituents independently selected from the group consisting of $(C_{1-4})$alkyl, $(C_{1-4})$alkoxy, trifluoromethyl, and halogen.

vi) According to a preferred variant of the embodiment v) above, the compounds of formula I or their salts (among which the pharmaceutically acceptable salts will be preferred) will be such that B represents phenyl which is unsubstituted or mono-substituted with methyl, fluorine or trifluoromethyl.

vii) According to one main embodiment of this invention, the compounds of formula I as defined in one of embodiments i) to vi) or their salts (among which the pharmaceutically acceptable salts will be preferred) will be such that n represents 0.

viii) According to another main embodiment of this invention, the compounds of formula I as defined in one of embodiments i) to vi) or their salts (among which the pharmaceutically acceptable salts will be preferred) will be such that n represents 1.

ix) According to yet another main embodiment of this invention, the compounds of formula I as defined in one of embodiments i) to viii) or their salts (among which the pharmaceutically acceptable salts will be preferred) will be such that $R^1$ represents one of the following groups:

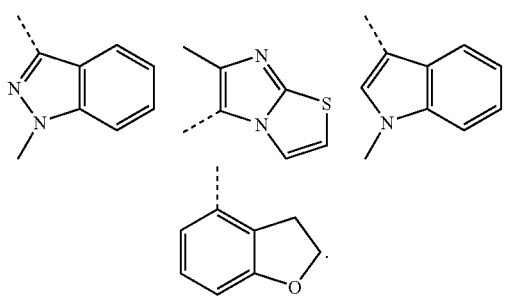

x) According to a variant of the main embodiment ix) above, the compounds of formula I as defined in one of embodiments i) to viii) or their salts (among which the pharmaceutically acceptable salts will be preferred) will be such that $R^1$ represents

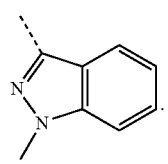

xi) According to another variant of the main embodiment ix) above, the compounds of formula I as defined in one of embodiments i) to viii), or their salts (among which the pharmaceutically acceptable salts will be preferred) will be such that R¹ represents

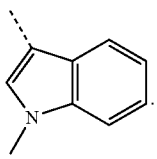

xii) According to a further variant of the main embodiment ix) above, the compounds of formula I as defined in one of embodiments i) to viii) or their salts (among which the pharmaceutically acceptable salts will be preferred) will be such that R¹ represents

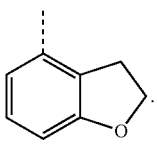

xiii) According to yet a further variant of the main embodiment ix) above, the compounds of formula I as defined in one of embodiments i) to viii) or their salts (among which the pharmaceutically acceptable salts will be preferred) will be such that R¹ represents

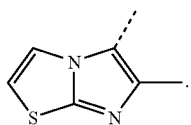

xiv) A further main embodiment of this invention relates to compounds of formula I as defined in one of embodiments i) to xiii) and to salts thereof (among which the pharmaceutically acceptable salts will be preferred), wherein A represents a pyridyl ring (in particular pyridin-4-yl or pyridin-3-yl).

xv) According to a variant of embodiment xiv), the compounds of the formula I or their salts (among which the pharmaceutically acceptable salts will be preferred) will be such that:
Y represents $(CH_2)_n$, wherein n represents 0 or 1;
B represents phenyl, wherein the phenyl ring is mono-substituted with $(C_{1-4})$alkyl (such as especially methyl), trifluoromethyl, or halogen (such as especially fluorine);
A represents a pyridyl ring; and
R¹ is selected from the following groups:

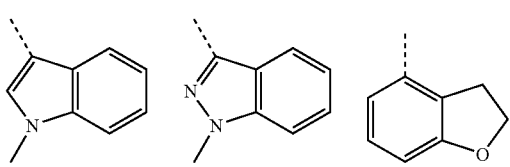

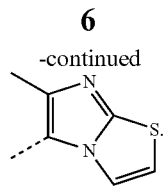

xvi) Yet a further main embodiment of the invention relates to compounds of formula I as defined in one of embodiments i) to xiii) and to salts thereof (among which the pharmaceutically acceptable salts will be preferred), wherein A represents phenyl which is unsubstituted or substituted once with methyl, fluorine or trifluoromethyl.

xvii) According to a variant of embodiment xvi), the compounds of formula I or their salts (among which the pharmaceutically acceptable salts will be preferred) will be such that:
Y represents $(CH_2)_n$, wherein n represents 0 or 1;
B represents phenyl which is mono-substituted with $(C_{1-4})$ alkyl (such as especially methyl), trifluoromethyl or halogen (such as especially fluorine);
A represents phenyl which is unsubstituted or mono-substituted with methyl, fluorine or trifluoromethyl; and
R¹ is selected from the following groups:

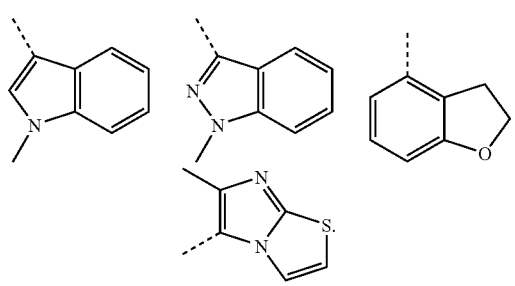

xviii) A particular embodiment of the invention relates to compounds of formula I as defined in one of embodiments i) to xiii) and to salts thereof (among which the pharmaceutically acceptable salts will be preferred), wherein:
Y represents $(CH_2)_n$, wherein n represents 0 or 1;
B represents phenyl which is mono-substituted with $(C_{1-4})$ alkyl (such as especially methyl), trifluoromethyl or halogen (such as especially fluorine);
A represents 3-pyridyl, 4-pyridyl or a phenyl ring wherein the phenyl ring is unsubstituted or mono-substituted with methyl, fluorine or trifluoromethyl; and
R¹ is selected from the following groups:

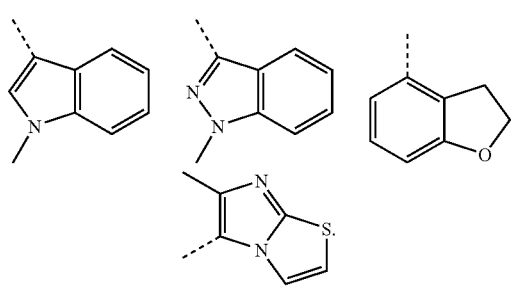

xix) Particularly preferred are the following compounds of formula I as defined in embodiment i) or ii):
(S)-6-methyl-imidazo[2,1-b]thiazole-5-carboxylic acid{1-[5-(4-fluoro-phenyl)-2-(2-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(3-fluoro-phenyl)-thiazole-4-carbonyl]-piperidin-2-ylmethyl}-amide;

(S)-6-methyl-imidazo[2,1-b]thiazole-5-carboxylic acid{1-[2,5-bis-(4-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(2-methoxy-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(3-methoxy-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(4-methoxy-phenyl)-thiazole-4-carbonyl]-piperidin-2-ylmethyl}-amide;

(S)-6-methyl-imidazo[2,1-b]thiazole-5-carboxylic acid{1-[2-(3,5-difluoro-phenyl)-5-(4-fluoro-phenyl)-thiazole-4-carbonyl]-piperidin-2-ylmethyl1-amide;

(S)-6-methyl-imidazo[2,1-b]thiazole-5-carboxylic acid{1-[2-(3,4-difluoro-phenyl)-5-(4-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-m-tolyl-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-p-tolyl-thiazole-4-carbonyl]-piperidin-2-ylmethyl}-amide;

(S)-6-methyl-imidazo[2,1-b]thiazole-5-carboxylic acid{1-[2-(2-fluoro-5-methyl-phenyl)-5-(4-fluoro-phenyl)-thiazole-4-carbonyl]-piperidin-2-ylmethyl1-amide;

(S)-6-methyl-imidazo[2,1-b]thiazole-5-carboxylic acid{1-[2(3-fluoro-4-methyl-phenyl)-5-(4-fluoro-phenyl)-thiazole-4-carbonyl]-piperidin-2-ylmethyl1-amide;

(S)-6-methyl-imidazo[2,1-b]thiazole-5-carboxylic acid{1[2-(4-fluoro-2-methyl-phenyl)-5-(4-fluoro-phenyl)-thiazole-4-carbonyl]-piperidin-2-ylmethyl1-amide;

(S)-6-methyl-imidazo[2,1-b]thiazole-5-carboxylic acid{1-[5-(4-fluoro-phenyl)-2-o-tolyl-thiazole-4-carbonyl]-piperidin-2-ylmethyl}-amide;

(S)-2,3-dihydro-benzofuran-4-carboxylic acid{1-[5-(2-fluoro-phenyl)-2-phenyl-thiazole-4-carbonyl]-piperidin-2-ylmethyl}-amide;

(S)-2,3-dihydro-benzofuran-4-carboxylic acid{1-[5-(2-fluoro-phenyl)-2-m-tolyl-thiazole-4-carbonyl]-piperidin-2-ylmethyl}-amide;

(S)-2,3-dihydro-benzofuran-4-carboxylic acid{1-[5-(2-fluoro-phenyl)-2-(3-fluoro-phenyl)-thiazole-4-carbonyl]-piperidin-2-ylmethyl}-amide;

(S)-2,3-dihydro-benzofuran-4-carboxylic acid{1-[5-(2-fluoro-phenyl)-2-(3-methoxy-phenyl)-thiazole-4-carbonyl]-piperidin-2-ylmethyl}-amide;

(S)-2,3-dihydro-benzofuran-4-carboxylic acid{1-[5-(2-fluoro-phenyl)-2-p-tolyl-thiazole-4-carbonyl]-piperidin-2-ylmethyl}-amide;

(S)-2,3-dihydro-benzofuran-4-carboxylic acid{1-[5-(2-fluoro-phenyl)-2-(4-fluoro-phenyl-thiazole-4-carbonyl]-piperidin-2-ylmethyl}-amide;

(S)-2,3-dihydro-benzofuran-4-carboxylic acid{1-[5-(2-fluoro-phenyl)-2-(4-methoxy-phenyl)-thiazole-4-carbonyl]-piperidin-2-ylmethyl}-amide;

(S)-1-methyl-1H-indole-3-carboxylic acid{1-[5-(2-fluoro-phenyl)-2-phenyl-thiazole-4-carbonyl]-piperidin-2-ylmethyl}-amide;

(S)-1-methyl-1H-indole-3-carboxylic acid{1-[5-(2-fluoro-phenyl)-2-m-tolyl-thiazole-4-carbonyl]-piperidin-2-ylmethyl}-amide;

(S)-1-methyl-1H-indole-3-carboxylic acid{1-[5-(2-fluoro-phenyl)-2-(3-fluoro-phenyl)-thiazole-4-carbonyl]-piperidin-2-ylmethyl}-amide;

(S)-1-methyl-1H-indole-3-carboxylic acid{1-[5-(2-fluoro-phenyl)-2-(3-methoxy-phenyl)-thiazole-4-carbonyl]-piperidin-2-ylmethyl}-amide;

(S)-1-methyl-1H-indole-3-carboxylic acid{1-[5-(2-fluoro-phenyl)-2-p-tolyl-thiazole-4-carbonyl]-piperidin-2-ylmethyl}-amide;

(S)-1-methyl-1H-indole-3-carboxylic acid{1-[5-(2-fluoro-phenyl)-2-(4-fluoro-phenyl)-thiazole-4-carbonyl]-piperidin-2-ylmethyl}-amide (S)-1-methyl-1H-indole-3-carboxylic acid{1-[5-(2-fluoro-phenyl)-2-(4-methoxy-phenyl)-thiazole-4-carbonyl]-piperidin-2-ylmethyl}-amide;

(S)-2,3-dihydro-benzofuran-4-carboxylic acid{1-[2-phenyl-5-(3-trifluoromethyl-phenyl)-thiazole-4-carbonyl]-piperidin-2-ylmethyl}-amide;

(S)-2,3-dihydro-benzofuran-4-carboxylic acid{1-[2-(3-fluoro-phenyl)-5-(3-trifluoromethyl-phenyl)-thiazole-4-carbonyl]-piperidin-2-ylmethyl}-amide;

(S)-2,3-dihydro-benzofuran-4-carboxylic acid{1-[2-(3-methoxy-phenyl)-5-(3-trifluoromethyl-phenyl)-thiazole-4-carbonyl]-piperidin-2-ylmethyl}-amide;

(S)-2,3-dihydro-benzofuran-4-carboxylic acid{1-[2-(4-fluoro-phenyl)-5-(3-trifluoromethyl-phenyl)-thiazole-4-carbonyl]-piperidin-2-ylmethyl}-amide;

(S)-6-methyl-imidazo[2,1-b]thiazole-5-carboxylic acid[1-(2-phenyl-5-p-tolyl-thiazole-4-carbonyl)-piperidin-2-ylmethyl]-amide;

(S)-2,3-dihydro-benzofuran-4-carboxylic acid{1-[5-(3-chloro-phenyl)-2-pyridin-4-yl-thiazole-4-carbonyl]-pyrrolidin-2-ylmethyl}-amide;

(S)-6-methyl-imidazo[2,1-b]thiazole-5-carboxylic acid{1-[5-(3-chloro-phenyl)-2-pyridin-4-yl-thiazole-4-carbonyl]-pyrrolidin-2-ylmethyl}-amide;

(S)-1-methyl-1H-indazole-3-carboxylic acid{1-[5-(3-chloro-phenyl)-2-pyridin-4-yl-thiazole-4-carbonyl]-pyrrolidin-2-ylmethyl}-amide;

(S)-6-methyl-imidazo[2,1-b]thiazole-5-carboxylic acid{1-[5-(3-chloro-phenyl)-2-pyridin-3-yl-thiazole-4-carbonyl]-pyrrolidin-2-ylmethyl}-amide;

(S)-benzofuran-4-carboxylic acid{1-[5-(3-chloro-phenyl)-2-pyridin-3-yl-thiazole-4-carbonyl]-pyrrolidin-2-ylmethyl}-amide;

(S)-1-methyl-1H-indazole-3-carboxylic acid{1-[5-(3-chloro-phenyl)-2-pyridin-3-yl-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-m-tolyl-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-p-tolyl-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-(2-fluoro-phenyl)-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-(3-fluoro-phenyl)-thiazole-4-carbonyl]-pyrrolidin-2-ylmethyl}-amide;

(S)-6-methyl-imidazo[2,1-b]thiazole-5-carboxylic acid{1-[2,5-bis-(4-fluoro-phenyl)-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-(2-methoxy-phenyl)-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-(3-methoxy-phenyl)-thiazole-4-carbonyl]-pyrrolidin-2-ylmethyl}-amide;

(S)-6-methyl-imidazo[2,1-b]thiazole-5-carboxylic acid{1-[5-(4-fluoro-phenyl)-2-(4-methoxy-phenyl)-thiazole-4-carbonyl]-pyrrolidin-2-ylmethyl}-amide;

and the salts (in particular pharmaceutically acceptable salts) thereof.

Where the plural form is used for compounds, salts, pharmaceutical compositions, diseases or the like, this is intended to mean also a single compound, salt, disease or the like.

Any reference to a compound of formula I is to be understood as referring also to salts (especially pharmaceutically acceptable salts) of a compound of formula I, respectively, as appropriate and expedient. Besides, any preferences indicated for the compounds of formula I (whether for the compounds themselves, salts thereof, compositions containing the compounds or salts thereof, uses of the compounds or salts thereof, etc.) apply *mutatis mutandis* to compounds of formula $I_{CE}$.

The compounds according to formula I may be used for the preparation of a medicament, and are suitable, for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

In a preferred embodiment, the compounds according to formula I may be used for the preparation of a medicament, and are suitable, for the prevention or treatment of diseases selected from the group consisting of all types of sleep disorders, of stress-related syndromes, of psychoactive substance use, abuse, seeking and reinstatement, of cognitive dysfunctions in the healthy population and in psychiatric and neurologic disorders, of eating or drinking disorders. Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance. Psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention, the compounds according to formula I may be used for the preparation of a medicament, and are suitable, for the prevention or treatment of diseases selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention, the compounds according to formula I may be used for the preparation of a medicament, and are suitable, for the prevention or treatment of diseases selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention, the compounds according to formula I may be used for the preparation of a medicament, and are suitable, for the prevention or treatment of diseases selected from the group consisting of eating disorders that comprise metabolic dysfunction; dysregulated appetite control; compulsive obesities; emeto-bulimia or anorexia nervosa.

In another preferred embodiment of the invention, the compounds according to formula I may be used for the preparation of a medicament, and are suitable, for the prevention or treatment of diseases selected from the group consisting of Psychoactive substance use, abuse, seeking and reinstatement that comprise all types of psychological or physical addictions and their related tolerance and dependence components.

The invention also relates to a pharmaceutical composition containing, as active principle, a compound of formula I or a pharmaceutically acceptable salt of such a compound, and at least one pharmaceutically acceptable carrier.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I and their pharmaceutically acceptable salts can be used as medicaments, e.g. in the form of pharmaceutical compositions for enteral or parenteral administration.

A further aspect of the invention is a process for the preparation of compounds of formula I. Compounds according to formula I of the present invention can be prepared according to the general sequence of reactions outlined in the schemes below wherein A, B, Y, n and $R^1$ are as defined in the description of formula I. The compounds obtained may also be converted into pharmaceutically acceptable salts thereof in a manner known per se.

In general, all chemical transformations can be performed according to well-known standard methodologies as described in the literature or as described in the procedures below.

Preparation of the Compounds of Formula I

Abbreviations:

The following abbreviations are used throughout the specification and the examples:

aq. aqueous
Boc tert-butoxycarbonyl
BSA bovine serum albumin
CHO Chinese hamster ovary
conc. concentrated
cy- cyclo-
DCM dichloromethane
DIBAL diisobutylaluminium hydride
DIPEA diisopropylethylamine
DME dimethoxyethane
DMF N,N-dimethylformamide
eq equivalent(s)
ES electron spray
Et ethyl
ether diethylether
EtOAc ethyl acetate
EtOH ethanol
FCS foetal calf serum
FLIPR fluorescent imaging plate reader
HBSS Hank's balanced salt solution
HEPES 4-(2-hydroxyethyl)-piperazine-1-ethanesulfonic acid
HPLC high performance liquid chromatography
HV high vacuum
iPrOH iso-propanol
KOtBu potassium tertiary (tert.) butoxide
LAH lithium aluminum hydride
LC Liquid chromatography
M molar(ity)
Me methyl
MeOH methanol
MS mass spectroscopy
org. organic
Ph phenyl
prep. preparative
RT room temperature
sat. saturated
$SiO_2$ silica gel
tBu tert-butyl
$t_R$ retention time
TBME tert-butyl methyl ether
TBTU O-benzotriazol-1-yl-N,N,N',N'-tetramethyluronium tetrafluoroborate
THF tetrahydrofuran General Preparation Methods:

Preparation of the Compounds of Formula I:

The compounds of formula I can be prepared for example according to the method outlined in Scheme 1 hereafter.

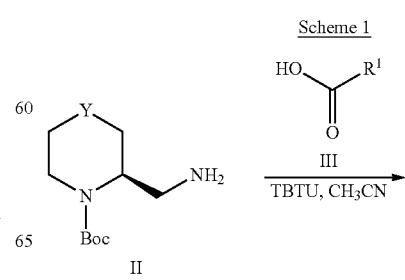

Scheme 1

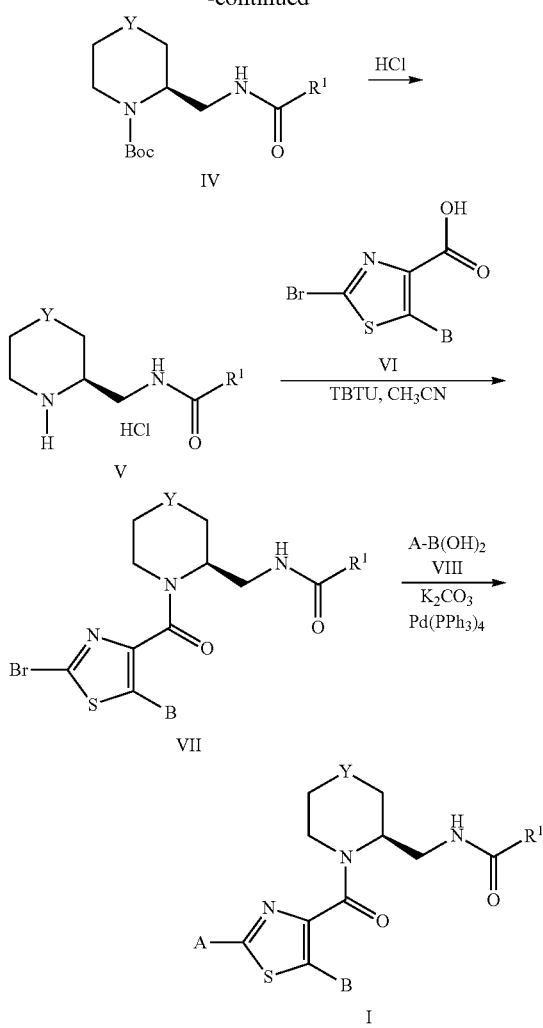

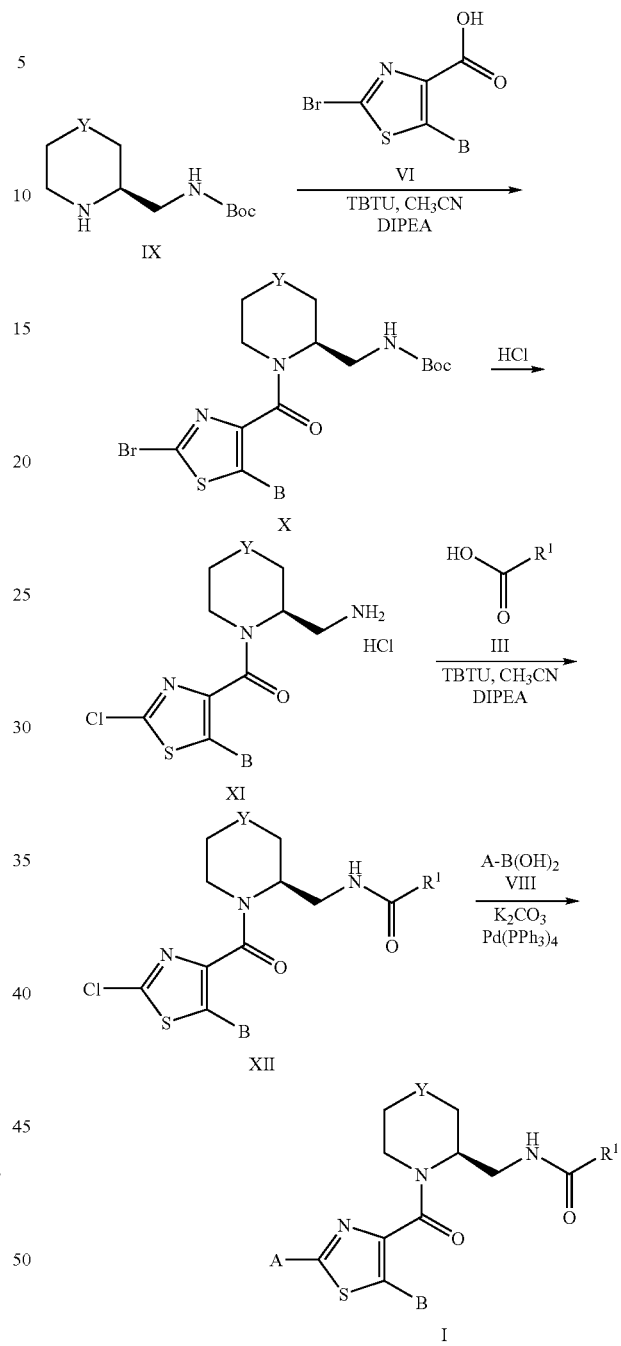

In Scheme 1, A, B, Y and $R^1$ are as defined in formula I.

According to the preparation pathway shown in Scheme 1, the synthesis of compounds of formula I can begin with commercially available compound of formula II which can be acylated with a commercially available carboxylic acid of formula III under standard reaction conditions with an activating agent such as TBTU in the presence of a base such as DIPEA in a solvent such as acetonitrile to give the intermediate of formula IV. Deprotection of the intermediate of formula IV under acidic conditions (e.g. HCl in dioxane) results in the secondary amine of formula V. Subsequent acylation with a 2-bromo-thiazole-4-carboxylic acid derivative of formula VI (see Schemes 5 and 6 for its preparation) yields the compound of formula VII. The last step of the sequence for the preparation of the compound of formula I consists in a Suzuki-reaction of the 2-bromo-thiazole precursor of formula VII with the commercially available aryl boronic acid of formula VIII under standard palladium-catalyzed conditions (e.g. using aq. $K_2CO_3$ and $Pd(PPh_3)_4$ in iPrOH/toluene - see experimental part for details).

The compounds of formula I can also be prepared according to the method summarised in Scheme 2 hereafter.

In Scheme 2, A, B, Y and $R^1$ are as defined in formula I.

According to the preparation pathway shown in Scheme 2, the sequence for the preparation of compounds of formula I can begin with a commercially available 2-aminomethyl substituted piperidine- or pyrrolidine-derivative of formula IX, Boc-protected at the exocyclic nitrogen atom. The compound of formula IX can be acylated with the 2-bromo-5-aryl-thiazole-4-carboxylic acid derivative of formula VI (see Scheme 3 and 4 preparation) under standard amide bond forming conditions to give the intermediate of formula X. Boc-deprotection yields the intermediate of formula XI and subsequent acylation with the commercially available carboxylic acid derivative of formula III yields the 2-chloro-thiazole containing precursor of formula XI. The last step of the sequence for the preparation of the compounds of formula I consists in a Suzuki-reaction of the 2-chloro-thiazole precursor of formula XI with the commercially available aryl boronic acid of formula VIII under standard palladium-catalyzed conditions (e.g. using aq. $K_2CO_3$ and $Pd(PPh_3)_4$ in iPrOH/toluene - see experimental part for details).

An alternative approach to prepare compounds of formula I is shown in Scheme 3 hereafter.

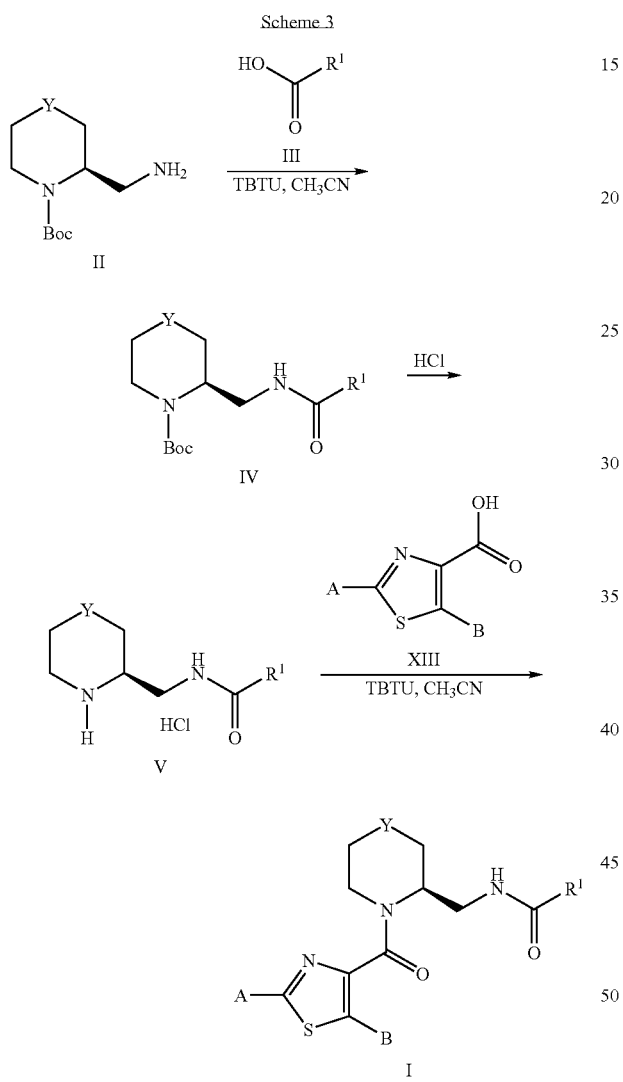

In Scheme 3, A, B, Y and $R^1$ are as defined in formula I.

According to the preparation pathway shown in Scheme 3, the synthesis of compounds of formula I can begin with the commercially available 1-Boc-2-aminomethyl-piperidine or—pyrrolidine of formula II which can be acylated with the commercially available carboxylic acid of formula III under standard reaction conditions with an activating agent such as TBTU in the presence of a base such as DIPEA in a solvent such as acetonitrile to give the intermediate of formula III. Deprotection of the intermediates of formula III under acidic conditions (e.g. HCl in dioxane) yields the secondary amine of formula IV. Subsequent acylation with a 2-aryl-5-aryl-thiazole-4-carboxylic acid derivative of formula XIII (see Schemes 5 and 6 for its preparation) gives the compound of formula I.

Another alternative approach to prepare compounds of formula I is shown in Scheme 4 hereafter.

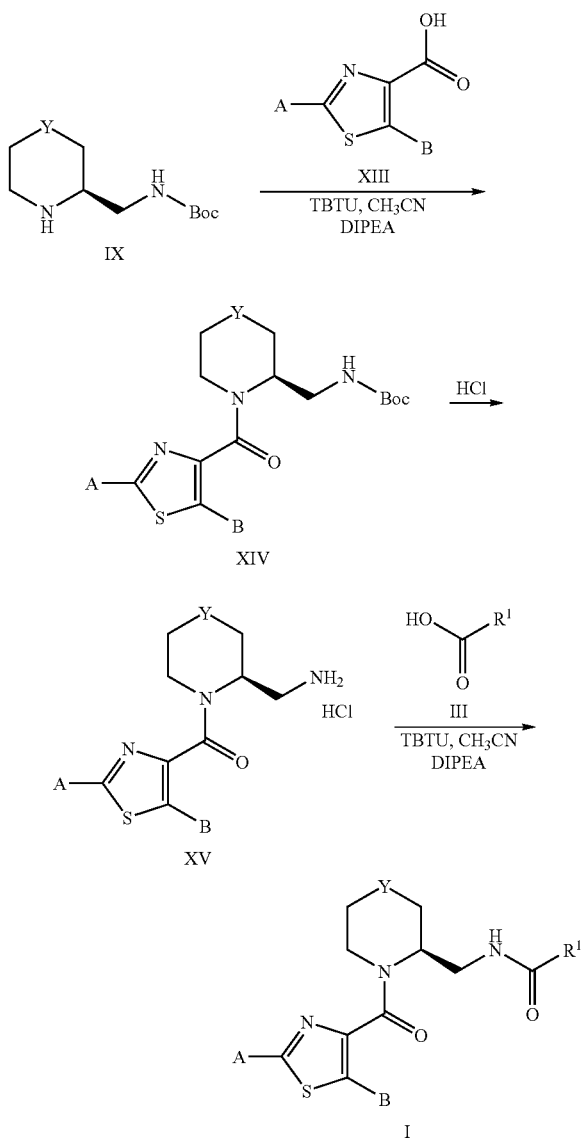

According to the preparation pathway shown in Scheme 4, the sequence for the preparation of compounds of formula I begins with a commercially available 2-aminomethyl substituted piperidine- or pyrrolidine-derivative of formula IX, Boc-protected at the exocyclic nitrogen atom. The compound of formula IX can be acylated with the 2-aryl-5-aryl-thiazole-4-carboxylic acid derivative of formula XIII (see Schemes 5 and 6 for its preparation) under standard amide bond forming conditions to give the intermediate of formula XIV. Boc-deprotection yields the intermediate of formula XV and subsequent acylation with the commercially available carboxylic acid derivative of formula III gives the final compound.

Preparation of the Intermediates of Formula XIII:

The compounds of formula XIII can for example be synthesised according to the method summarised in Scheme 5.

Scheme 5

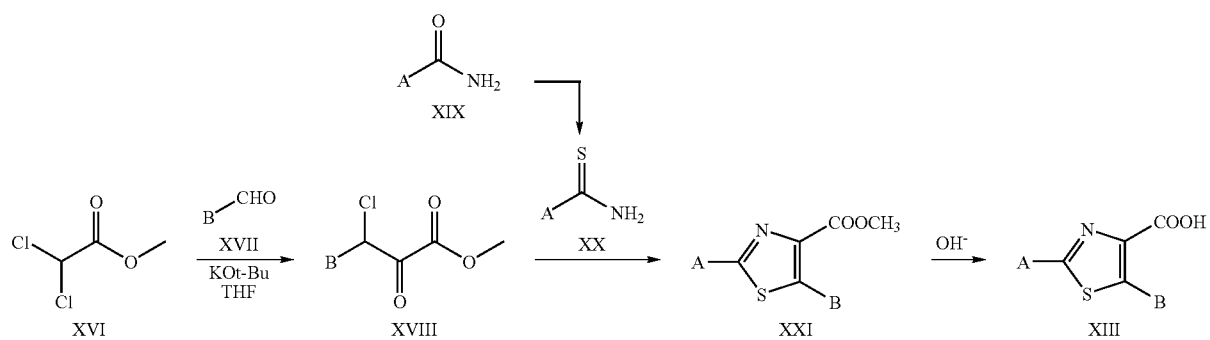

In Scheme 5, A and B are as defined in formula I.

By reaction of methyl dichloroacetate (XVI) (commercially available) with the aldehyde of formula XVII (usually commercially available; if not, see next paragraph) in the presence of a base like potassium tert-butoxide (KOtBu), the α-oxo-ester derivative of formula XVIII can be obtained, which can be transformed in a reaction with an aryl-thiocarbamide of formula XX (prepared from commercially available aryl-carboxamide of formula XIX with Lawesson's reagent) into a thiazole derivative of formula XXI. Hydrolysis of the ester function with an aqueous solution of e.g. sodium hydroxide in a solvent like MeOH or iPrOH yields the carboxylic acid of formula XIII.

The aldehydes of formula XVII, if not commercially available, can be synthesized by any procedure known from the literature like for example reduction of the respective carboxylic acid or their different derivatives with a reducing agent, by reduction of the respective nitrile or by oxidation of benzylic alcohols and their heterocyclic analogues with oxidating agents (e.g.: J. March, *Advanced Organic Chemistry*, 4th edition, John Wiley & Sons, p. 447-449, 919-920 and 1167-1171).

Alternatively, the compounds of formula XIII can also be prepared according to the method summarised in Scheme 6.

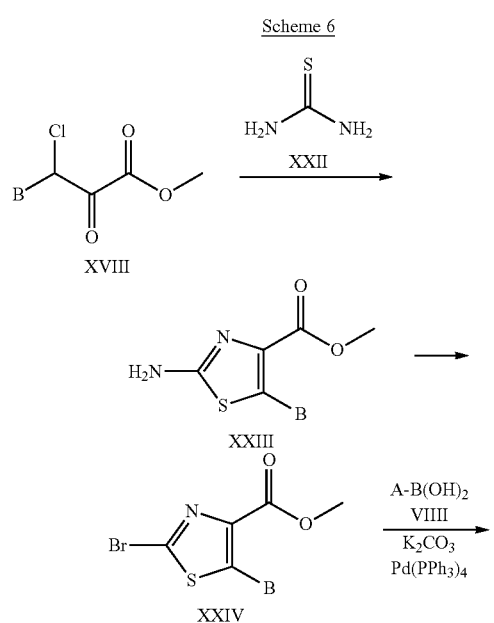

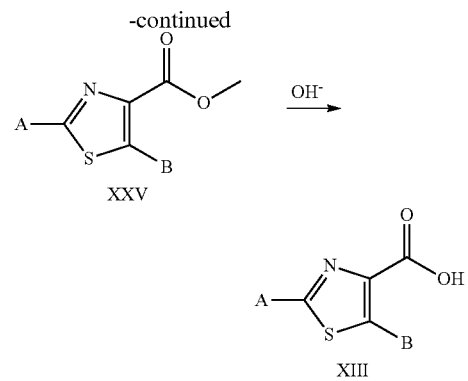

In Scheme 6, A and B are as defined in formula I.

Following this method, the α-oxo-ester derivative of formula XVIII (obtained as described in Scheme 5) can be condensed with thiourea (XXII) using a Hantzsch cyclization step to obtain the 2-amino-thiazole intermediate of formula XIII which can be transformed into the 2-bromo-thiazole compound of formula XXIV by a classical Sandmeyer reaction (e.g. using $CuBr_2$ and iso-amyl nitrite in a solvent such as acetonitrile). The introduction of the aryl unit A can be achieved by the Pd-catalyzed Suzuki-coupling (e.g. using aq. $K_2CO_3$ and $Pd(PPh_3)_4$ in iPrOH/toluene) with the respective boronic acid of formula VIII (commercially available) to give the 2-aryl-thiazole-derivative of formula XXV which can be transformed into the compound of formula XIII according to the method described in Scheme 5.

Particular embodiments of the invention are described in the following Examples, which serve to illustrate the invention in more detail without limiting its scope in any way.

EXPERIMENTAL SECTION

Chemistry:

The following examples illustrate the preparation of pharmacologically active compounds of the invention but do not at all limit the scope thereof.

All temperatures are stated in ° C. Compounds are characterized by:

$^1$H-NMR:

300 MHz Varian Oxford or 400 MHz Bruker Avance; chemical shifts are given in ppm relative to the solvent used; multiplicities: s=singlet, d=doublet, t=triplet, m=multiplet, b=broad, coupling constants are given in Hz.

LC-MS:

Device: Agilent 1100 series with DAD and MS detection (MS: Finnigan single quadrupole); Columns (4.6×50 mm, 5

μm): Zorbax SB-AQ, Zorbax Extend C18 or Waters XBridge C18; Conditions (if not otherwise stated the acidic gradient is used):

basic: eluent A: MeCN, eluent B: conc. $NH_3$ in water (1.0 mL/L), 5% to 95% $CH_3CN$;

acidic: eluent A: MeCN, eluent B: TFA in water (0.4 mL/L), 5% to 95% $CH_3CN$), $t_R$ is given in min.

Compounds are purified by column chromatography on $SiO_2$ or by preparative HPLC using RP-$C_{18}$ based columns with MeCN/water gradients and formic acid or ammonia additives.

A. Preparation of Precursors and Intermediates:

A.1 Synthesis of thiazole-4-carboxylic acid derivatives:

A.1.1 Synthesis of 3-chloro-2-oxo-propionic ester derivatives ("Darzens-reaction")

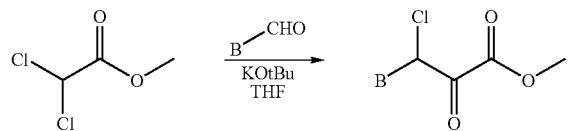

A solution of the respective aldehyde (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred overnight and concentrated in vacuo. DCM and ice-cold water are added, the layers are separated and the aqueous layer is extracted twice with DCM. The combined org. layers are washed with ice-cold water and brine, dried over $MgSO_4$ and concentrated in vacuo to give the desired α-oxo-ester which is used without further purification.

The following compounds are prepared according to the procedure outlined above:

3-chloro-2-oxo-3-m-tolyl-propionic acid methyl ester
prepared by reaction of 3-methyl-benzaldehyde with methyl dichloroacetate.

3-chloro-2-oxo-3-p-tolyl-propionic acid methyl ester
prepared by reaction of 4-methyl-benzaldehyde with methyl dichloroacetate.

3-chloro-3-(3-fluoro-phenyl)-2-oxo-propionic acid methyl ester
prepared by reaction of 3-fluoro-benzaldehyde with methyl dichloroacetate.

3-chloro-3-(4-fluoro-phenyl)-2-oxo-propionic acid methyl ester
prepared by reaction of 4-fluoro-benzaldehyde with methyl dichloroacetate.

3-chloro-3-(2-fluoro-phenyl)-2-oxo-propionic acid methyl ester
prepared by reaction of 2-fluoro-benzaldehyde with methyl dichloro-acetate.

3-chloro-3-(3-chloro-phenyl)-2-oxo-propionic acid methyl ester
prepared by reaction of 3-chloro-benzaldehyde with methyl dichloro-acetate.

3-chloro-3-(3-trifluoromethyl-phenyl)-2-oxo-propionic acid methyl ester
prepared by reaction of 2-methyl-benzaldehyde with methyl dichloro-acetate.

A.1.2 Synthesis of 2-amino-thiazole-4-carboxylic acid methyl ester derivatives ("Hantzsch-reaction"):

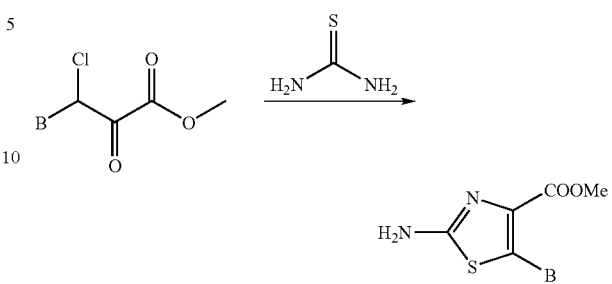

A solution of the respective α-oxo-ester (22.1 mmol, 1.0 eq) in acetone (25 mL) is added to a suspension of thiourea (22.1 mmol, 1.0 eq) in acetone (45 mL). The mixture is heated to 57° C. (bath temperature), stirred for 24 h and concentrated to half of the volume. The obtained suspension is filtered and the residue is washed with acetone. After drying the desired amino-thiazole derivative is obtained as a solid.

The following compounds are prepared according to the procedure outlined above:

2-amino-5-m-tolyl-thiazole-4-carboxylic acid methyl ester
prepared by reaction of 3-chloro-2-oxo-3-m-tolyl-propionic acid methyl ester with thiourea. LC-MS: $t_R$=0.78 min; $[M+H]^+$=249.0.

2-amino-5-p-tolyl-thiazole-4-carboxylic acid methyl ester
prepared by reaction of 3-chloro-2-oxo-3-p-tolyl-propionic acid methyl ester with thiourea. LC-MS: $t_R$=0.77 min; $[M+H]^+$=249.33.

2-amino-5-(3-fluoro-phenyl)-thiazole-4-carboxylic acid methyl ester
prepared by reaction of 3-chloro-3-(3-fluoro-phenyl)-2-oxo-propionic acid methyl ester with thiourea. LC-MS: $t_R$=0.76 min; $[M+H]^+$=253.27.

2-amino-5-(4-fluoro-phenyl)-thiazole-4-carboxylic acid methyl ester
prepared by reaction of 3-chloro-3-(4-fluoro-phenyl)-2-oxo-propionic acid methyl ester with thiourea. LC-MS: $t_R$=0.0.75 min; $[M+H]^+$=253.17.

2-amino-5-(2-fluoro-phenyl)-thiazole-4-carboxylic acid methyl ester
prepared by reaction of 3-chloro-3-(2-fluoro-phenyl)-2-oxo-propionic acid methyl ester with thiourea. LC-MS: $t_R$=0.76 min; $[M+H]^+$=253.20.

2-amino-5-(3-chloro-phenyl)-thiazole-4-carboxylic acid methyl ester
prepared by reaction of 3-chloro-3-(3-chloro-phenyl)-2-oxo-propionic acid methyl ester with thiourea. LC-MS: $t_R$=0.82 min; $[M+H]^+$=269.18.

2-amino-5-(3-trifluoromethyl-phenyl)-thiazole-4-carboxylic acid methyl ester
prepared by reaction of 3-chloro-3-(3-chloro-phenyl)-2-oxo-propionic acid methyl ester with thiourea. LC-MS: $t_R$=0.86 min; $[M+H]^+32$ 303.18.

A.1.3 Synthesis of 2-bromo-5-m-tolyl-thiazole-4-carboxylic acid methyl ester ("Sandmeyer-reaction")

Under nitrogen atmosphere 2-amino-5-m-tolyl-thiazole-4-carboxylic acid methyl ester (7.10 mmol) is added portion-wise to a mixture of $CuBr_2$ (7.10 mmol), isoamyl nitrite (10.6 mmol) and acetonitrile (30 mL) at 15° C. After 20 min the mixture is heated to 40° C. for 30 min and to 65° C. for 90 min. The volatiles are removed in vacuo and the residue is purified by flash chromatography (SiO$_2$, DCM to DCM/MeOH 98/2) to give the desired product. LC-MS: $t_R$=1.01 min; [M+H]$^+$=311.8.

The following compounds are prepared according to the procedure outlined above from the corresponding 2-aminothiazole derivatives:

2-bromo-5-p-tolyl-thiazole-4-carboxylic acid methyl ester
LC-MS: $t_R$=1.00 min; [M+H]$^+$=314.25.
2-bromo-5-(3-fluoro-phenyl)-thiazole-4-carboxylic acid methyl ester
LC-MS: $t_R$=0.97 min; [M+H]$^+$=316.17.
2-bromo-5-(4-fluoro-phenyl)-thiazole-4-carboxylic acid methyl ester
LC-MS: $t_R$=0.97 min; [M+H]$^+$=316.09.
2-bromo-5-(2-fluoro-phenyl)-thiazole-4-carboxylic acid methyl ester
LC-MS: $t_R$=0.96 min; [M+H]$^+$=316.11.
2-bromo-5-(3-chloro-phenyl)-thiazole-4-carboxylic acid methyl ester
LC-MS: $t_R$=1.00 min; [M+H]$^+$=332.17.
2-bromo-5-(3-trifluoromethyl-phenyl)-thiazole-4-carboxylic acid methyl ester
LC-MS: $t_R$=1.03 min; [M+H]$^+$=366.17.

A.1.4 Synthesis of 2-bromo-thiazole-4-carboxylic acids (ester hydrolysis):

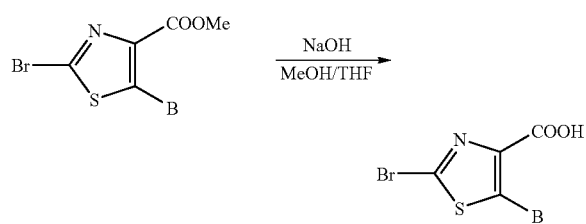

A solution of the respective ester (96.2 mmol) in a mixture of THF (150 mL) and MeOH (50 mL) is treated with an aq. NaOH solution (1.0 M, 192 mL). After stirring for 3 h, a white suspension is formed and the org. volatiles are removed in vacuo. The remaining mixture is diluted with water (100 mL), cooled in an ice-bath and made acidic (pH=3-4) by addition of aq. HCl solution (1.0 M). The suspension is filtered and the residue is washed with cold water. After drying the desired acid is obtained as a white solid.

The following compounds are prepared according to the procedure outlined above:
2-bromo-5-m-tolyl-thiazole-4-carboxylic acid
prepared by saponification of 2-bromo-5-m-tolyl-thiazole-4-carboxylic acid methyl ester.
LC-MS: $t_R$=0.89 min; [M+H]$^+$=298.20.
2-bromo-5-p-tolyl-thiazole-4-carboxylic acid
prepared by saponification of 2-bromo-5-p-tolyl-thiazole-4-carboxylic acid methyl ester.
LC-MS: $t_R$=0.89 min; [M+H$^+$=300.23.
2-bromo-5-(3-fluoro-phenyl)-thiazole-4-carboxylic acid
prepared by saponification of 2-bromo-5-(3-fluoro-phenyl)-thiazole-4-carboxylic acid methyl ester. LC-MS: $t_R$=0.87 min; [M+H]$^+$=302.12.
2-bromo-5-(4-fluoro-phenyl)-thiazole-4-carboxylic acid
prepared by saponification of 2-bromo-5-(4-fluoro-phenyl)-thiazole-4-carboxylic acid methyl ester. LC-MS: $t_R$=0.91 min; [M+H]$^+$=302.06.
2-bromo-5-(2-fluoro-phenyl)-thiazole-4-carboxylic acid
prepared by saponification of 2-bromo-5-(2-fluoro-phenyl)-thiazole-4-carboxylic acid methyl ester. LC-MS: $t_R$=0.85 min; [M+H]$^+$=302.12.
2-bromo-5-(3-chloro-phenyl)-thiazole-4-carboxylic acid
prepared by saponification of 2-bromo-5-(3-chloro-phenyl)-thiazole-4-carboxylic acid methyl ester. LC-MS: $t_R$=0.90 min; [M+H]$^+$=318.05.
2-bromo-5-(3-trifluoromethyl-phenyl)-thiazole-4-carboxylic acid
prepared by saponification of 2-bromo-5-(3-trifluoromethyl-phenyl)-thiazole-4-carboxylic acid methyl ester. LC-MS: $t_R$=0.93 min; [M+H]$^+$=352.19.

A.1.5. Synthesis of 2,5-bis-(hetero)aryl-thiazole-4-carboxylic acids ("Suzuki-reaction"):
5-(3-chloro-phenyl)-2-pyridin-4-yl-thiazole-4-carboxylic acid 2-bromo-5-(3-chloro-phenyl)-thiazole-4-carboxylic acid methyl ester (1.0 g, 3.0 mmol) was dissolved in a mixture of iPrOH (10 ml) and toluene (10 ml). An aqueous solution of K$_2$CO$_3$ (2M, 7.5 ml) was added followed by 4-pyridineboronic acid (370 mg, 3.0 mmol). The mixture was degassed by bubbling argon through it for 4 min, followed by the addition of tetrakis-triphenylphosphine palladium (104 mg, 0.09 mmol). The mixture was heated to 80° C. for 18 h, then an aq. NaOH solution (1M, 10 ml) was added and stirring continued at 80° C. for 60 min. The reaction mixture was concentrated under reduced pressure, followed by the addition of water (100 ml). The aq. phase was washed with ether (2×50 ml) and acidified to pH=4 by aq. HCl (1M). The precipitated product was filtered off and washed with cold water (10 ml) and finally purified by chromatography (SiO$_2$; DCM/MeOH=95/5) to give 217 mg of the expected product. LC-MS: $t_R$=0.75 min; [M+H]$^-$=316.98.
5-(3-chloro-phenyl)-2-pyridin-3-yl-thiazole-4-carboxylic acid
According to the procedure described above, except that 3-pyridineboronic acid replaced 4-pyridineboronic acid, 5-(3-chloro-phenyl)-2-pyridin-3-yl-thiazole-4-carboxylic acid was prepared. LC-MS: $t_R$=0.87 min; [M+H]$^+$=317.30.

B. Preparation of Compounds of Formula I:

Example 1

(S)-6-methyl-imidazo[2,1-b]thiazole-5-carboxylic acid{1-[5-(4-fluoro-phenyl)-2-(2-fluoro-phenyl)-thiazole-4-carbonyl]-piperidin-2-ylmethyl}-amide 1.1. (S)-{1-[2-bromo-5-(4-fluoro-phenyl)-thiazole-4-carbonyl]-piperidin-2-ylmethyl}-carbamic acid tert-butyl ester 2-bromo-5-(4-fluoro-phenyl)-thiazole-4-carboxylic acid (1.02 g, 3.38 mmol) was dissolved in acetonitrile (20 ml) followed by the addition of TBTU (1.19 g, 3.72 mmol) and DIPEA (547 mg, 4.22 mmol). Stirring was continued for 30 min. at rt. A solution of (S)-piperidin-2-ylmethyl-carbamic acid tert-butyl ester (725 mg, 3.38 mmol) in acetonitrile (20 ml) was added to the reaction mixture within 10 minutes and stiring was continued at rt for 24 h. The reaction mixture was concentrated under reduced pressure followed by the addition of aq. HCl (0.5 M, 50 ml). Stirring was continued for 30 min. The precipitated product was filtered off, washed with cold water and dried at HV to give the expected product (1.57 g). LC-MS: $t_R$=1.03 min; [M+H]$^+$=500.38.

1.2. (S)-(2-aminomethyl-piperidin-1-yl)-[2-chloro-5-(4-fluoro-phenyl)-thiazol-4-yl]-methanone Hydrochloride:

Intermediate 1.1 (1.56 g, 3.13 mmol) was dissolved in dioxane (5 ml) and HCl in dioxane (4M, 7.8 ml) was added.

Stirring was continued for 1 h at rt. The reaction mixture was evaporated to dryness and the residue dried under high vacuum to give 1.57 g of the expected compound. LC-MS: $t_R$=0.73 min; $[M+H]^+$=354.37. (the bromo-substituent in 2-position of the thiazole ring has been replaced by a chloro-substituent under Boc-deprotection conditions as described above).

1.3. (S)-6-methyl-imidazo[2,1-b]thiazole-5-carboxylic acid{1-[2-chloro-5-(4-fluoro-phenyl)-thiazole-4-carbonyl]-piperidin-2-ylmethyl}-amide:

6-methylimidazo[2,1-b][1,3]thiazole carboxylic acid (596 mg, 3.27 mmol) was dissolved in acetonitrile (20 ml) followed by the addition of TBTU (1.155 g, 3.6 mmol) and DIPEA (2.11 g, 16.35 mmol). Stirring was continued for 15 min at rt. A solution of intermediate 1.2 (1.54 g, 3.27 mmol) in acetonitrile (20 ml) was added within 10 min. Stirring was continued for 20 h at RT. The reaction mixture was concentrated under reduced pressure followed by the addition of aq. hydrochloric acid (1M, 100 ml). The aqueous phase was washed with ether (2×30 ml) followed by the addition of aq. NaOH solution (1 M) to pH=9. The product precipitated and was filtered off, washed with cold water and dried under HV to give the expected compound (1.58 g). LC-MS: $t_R$=0.84 min; $[M+H]^-$=518.38.

1.4. (S)-6-methyl-imidazo[2,1-b]thiazole-5-carboxylic acid{1-[5-(4-fluoro-phenyl)-2-(2-fluoro-phenyl)-thiazole-4-carbonyl]-piperidin-2-ylmethyl}-amide:

Intermediate 1.3 (52 mg, 0.1 mmol) was dissolved in a 1/1-mixture of toluene/iPrOH (1 ml), followed by the addition of an aqueous solution of $K_2CO_3$ (1M, 0.25 ml) and 2-fluoro-benzeneboronic acid (14 mg, 0.1 mmol). The reaction mixture was deoxygenated by bubbling argon through it for 5 min, followed by the addition of tetrakis-triphenylphosphine palladium (3.5 mg, 0.003 mmol) and heating to 80° C. for 4 h. The reaction mixture was cooled to RT. The product was extracted with ether. The solvent was evaporated under reduced pressure and the residue was purified by preparative HPLC to give the expected compound (13 mg). LC-MS: $t_R$=0.91 min; $[M+H]^+$=578.20.

Examples 2 to 16 were prepared according to the sequence described for the preparation of the compound of Example 1, using however different aryl boronic acids in the $4^{th}$ step.

Example 2

(S)-6-methyl-imidazo[2,1-b]thiazole-5-carboxylic acid{1-[5-(4-fluoro-phenyl)-2-(3-fluoro-phenyl)-thiazole-4-carbonyl]-piperidin-2-ylmethyl}-amide LC-MS: $t_R$=0.90 min; $[M+H]^+$=578.21.

Example 3

(S)-6-methyl-imidazo[2,1-b]thiazole-5-carboxylic acid{1-[2,5-bis-4-fluoro-phenyl)-thiazole-4-carbonyl]-piperidin-2-ylmethyl}-amide LC-MS: $t_R$=0.90 min; $[M+H]^+$=578.20.

Example 4

(S)-6-methyl-imidazo[2,1-b]thiazole-5-carboxylic acid{1-[5-(4-fluoro-phenyl)-2-(2-methoxy-phenyl)-thiazole-4-carbonyl]-piperidin-2-ylmethyl}-amide LC-MS: $t_R$=0.89 min; $[M+H]^+$=590.21.

Example 5

(S)-6-methyl-imidazo[2,1-b]thiazole-5-carboxylic acid{1-[5-(4-fluoro-phenyl)-2-(3-methoxy-phenyl)-thiazole-4-carbonyl]-piperidin-2-ylmethyl}-amide LC-MS: $t_R$=0.89 min; $[M+H]^+$=590.22.

Example 6

(S)-6-methyl-imidazo[2,1-b]thiazole-5-carboxylic acid{1-[5-(4-fluoro-phenyl)-2-(4-methoxy-phenyl)-thiazole-4-carbonyl]-piperidin-2-ylmethyl}-amide LC-MS: $t_R$=0.89 min; $[M+H]^+$=590.21.

Example 7

(S)-6-methyl-imidazo[2,1-b]thiazole-5-carboxylic acid{1-[2-(3,5-difluoro-phenyl)-5-(4-fluoro-phenyl)-thiazole-4-carbonyl]-piperidin-2-ylmethyl}-amide LC-MS: $t_R$=1.00 min; $[M+H]^+$=596.12.

Example 8

(S)-6-methyl-imidazo[2,1-b]thiazole-5-carboxylic acid{1-[2-(3,4-difluoro-phenyl)-5-(4-fluoro-phenyl)-thiazole-4-carbonyl]-piperidin-2-ylmethyl}-amide LC-MS: $t_R$=0.98 min; $[M+H]^+$=596.07.

Example 9

(S)-6-methyl-imidazo[2,1-b]thiazole-5-carboxylic acid{1-[5-(4-fluoro-phenyl)-2-m-tolyl-thiazole-4-carbonyl]-piperidin-2-ylmethyl}-amide LC-MS: $t_R$=0.92 min; $[M+H]^+$=574.23.

Example 10

(S)-6-methyl-imidazo[2,1-b]thiazole-5-carboxylic acid{1-[5-(4-fluoro-phenyl)-2-p-tolyl-thiazole-4-carbonyl]-piperidin-2-ylmethyl}-amide LC-MS: $t_R$=0.91 min; $[M+H]^+$=574.24.

Example 11

(S)-6-methyl-imidazo[2,1-b]thiazole-5-carboxylic acid{1-[2-(3-fluoro-4-methoxy-phenyl)-5-(4-fluoro-phenyl)-thiazole-4-carbonyl]-piperidin-2-ylmethyl}-amide LC-MS: $t_R$=0.97 min; $[M+H]^+$=607.20.

Example 12

(S)-6-methyl-imidazo[2,1-b]thiazole-5-carboxylic acid{1-[2-(2-fluoro-5-methyl-phenyl)-5-(4-fluoro-phenyl)-thiazole-4-carbonyl]-piperidin-2-ylmethyl}-amide LC-MS: $t_R$=1.02 min; [M+H]$^+$=592.11.

Example 13

(S)-6-methyl-imidazo[2,1-b]thiazole-5-carboxylic acid{1-[2-(3-fluoro-4-methyl-phenyl)-5-(4-fluoro-phenyl)-thiazole-4-carbonyl]-piperidin-2-ylmethyl}-amide LC-MS: $t_R$=1.01 min; [M+H]$^+$=592.11.

Example 14

(S)-6-methyl-imidazo[2,1-b]thiazole-5-carboxylic acid{1-[2-(4-fluoro-2-methyl-phenyl)-5-(4-fluoro-phenyl)-thiazole-4-carbonyl]-piperidin-2-ylmethyl}-amide LC-MS: $t_R$=0.98 min; [M+H]$^+$=592.11.

Example 15

(S)-6-methyl-imidazo[2,1-b]thiazole-5-carboxylic acid{1-[5-(4-fluoro-phenyl)-2-phenyl-thiazole-4-carbonyl]-piperidin-2-ylmethyl}-amide LC-MS: $t_R$=0.94 min; [M+H]$^+$=560.05.

Example 16

(S)-6-methyl-imidazo[2,1-b]thiazole-5-carboxylic acid{1-[5-(4-fluoro-phenyl)-2-o-tolyl-thiazole-4-carbonyl]-piperidin-2-ylmethyl}-amide LC-MS: $t_R$=0.90 min; [M+H]$^+$=574.22.

Example 17

(S)-2,3-dihydro-benzofuran-4-carboxylic acid{1-[5-(2-fluoro-phenyl)-2-phenyl-thiazole-4-carbonyl]-piperidin-2-ylmethyl}-amide

17.1. (S)-{1-[2-bromo-5-(2-fluoro-phenyl)-thiazole-4-carbonyl]-piperidin-2-ylmethyl}-carbamic acid tent-butyl ester:

This compound was prepared using a method analogous to that of Example 1, step 1.1. LC-MS: $t_R$=1.04 min; [M+H]$^+$=498.08.

17.2. (S)-(2-aminomethyl-piperidin-1-yl)-[2-bromo-5-(2-fluoro-phenyl)-thiazol-4-yl]-methanone:

Intermediate 17.1 (4.2 g, 5.0 mmol) was dissolved in DCM (36 ml) followed by the addition of TFA (4 ml). Stirring was continued for 6 h at RT. DCM (50 ml) and water (50 ml) were added to the reaction mixture and the phases were separated. The aq. phase was extracted again with DCM (50 ml), the combined org. layers were washed with brine (80 ml), dried over MgSO$_4$, filtered and concentrated under reduced pressure to give the expected product (2.4 g). LC-MS: $t_R$=0.74 min; [M+H]$^+$=397.98.

17.3. (S)-2,3-dihydro-benzofuran-4-carboxylic acid{142-bromo-5-(2-fluoro-phenyl)-thiazole-4-carbonyl]-piperidin-2-ylmethyl}-amide:

This compound was prepared from intermediate 17.2 using a method analogous to that of Example 1, step 1.3. LC-MS: $t_R$=1.05 min; [M+H]$^+$=545.37.

17.4. (S)-2,3-dihydro-benzofuran-4-carboxylic acid{1-[5-(2-fluoro-phenyl)-2-phenyl-thiazole-4-carbonyl]-piperidin-2-ylmethyl}-amide:

This compound was prepared from intermediate 17.3 using a method analogous to that of Example 1, step 1.4. LC-MS: $t_R$=1.11 min; [M+H]$^+$=542.13.

Examples 18 to 24 were prepared according to the sequence described for the preparation of the compound of Example 17, using however different aryl boronic acids in the 4$^{th}$ step.

Example 18

(S)-2,3-dihydro-benzofuran-4-carboxylic acid{1-[5-(2-fluoro-phenyl)-2-m-tolyl-thiazole-4-carbonyl]-piperidin-2-ylmethyl}-amide LC-MS: $t_R$=1.14 min; [M+H$^+$=556.15.

example 19

(S)-2,3-dihydro-benzofuran-4-carboxylic acid{1-[5-(2-fluoro-phenyl)-2-(3-fluoro-phenyl)-thiazole-4-carbonyl]-piperidin-2-ylmethyl}-amide LC-MS: $t_R$=1.11 min; [M+H]$^+$=560.14.

Example 20

(5)-2,3-dihydro-benzofuran-4-carboxylic acid{1-[5-(2-fluoro-phenyl)-2-(3-methoxy-phenyl)-thiazole-4-carbonyl]-piperidin-2-ylmethyl}-amide LC-MS: $t_R$=1.21 min; [M+H]$^+$=572.07.

Example 21

(S)-2,3-dihydro-benzofuran-4-carboxylic acid{1-[5-(2-fluoro-phenyl)-2-p-tolyl-thiazole-4-carbonyl]-piperidin-2-ylmethyl}-amide LC-MS: $t_R$=1.14 min; [M+H]$^+$=556.13.

Example 22

(S)-2,3-dihydro-benzofuran-4-carboxylic acid{1-[5-(2-fluoro-phenyl)-2-(4-fluoro-phenyl)-thiazole-4-carbonyl]-piperidin-2-ylmethyl}-amide LC-MS: $t_R$=1.12 min; [M+H]$^+$=560.08.

Example 23

(S)-2,3-dihydro-benzofuran-4-carboxylic acid{1-[5-(2-fluoro-phenyl)-2-(4-methoxy-phenyl)-thiazole-4-carbonyl]-piperidin-2-ylmethyl}-amide LC-MS: $t_R$=1.11 min; [M+H]$^+$=572.07.

Example 24

(S)-1-methyl-1H-indole-3-carboxylic acid{1-[5-(2-fluoro-phenyl)-2-phenyl-thiazole-4-carbonyl]-piperidin-2-ylmethyl}-amide 24.1. 1-methyl-1H-indole-3-carboxylic acid{1-[2-bromo-5-(2-fluoro-phenyl)-thiazole-4-carbonyl]-piperidin-2-ylmethyl}-amide:

This compound was prepared from intermediate 17.2 using a method analogous to that of Example 1, step 1.3. LC-MS: $t_R$=1.05 min; [M+H]$^+$=556.95.

24.2. (S)-1-methyl-1H-indole-3-carboxylic acid{1-[5-(2-fluoro-phenyl)-2-phenyl-thiazole-4-carbonyl]-piperidin-2-ylmethyl}-amide:

This compound was prepared from intermediate 24.1 using a method analogous to that of Example 1, step 1.4. LC-MS: $t_R$=1.11 min; [M+H]$^+$=553.21.

Examples 25 to 30 were prepared according to the sequence described for the preparation of the compound of Example 24, using however different aryl boronic acids in the 2$^{nd}$ step.

Example 25

(S)-1-methyl-1H-indole-3-carboxylic acid{1-[5-(2-fluoro-phenyl)-2-m-tolyl-thiazole-4-carbonyl]-piperidin-2-ylmethyl}-amide:

LC-MS: $t_R$=1.14 min; [M+H]$^+$=567.10.

Example 26

(S)-1-methyl-1H-indole-3-carboxylic acid{1-[5-(2-fluoro-phenyl)-2-(3-fluoro-phenyl)-thiazole-4-carbonyl]-piperidin-2-ylmethyl}-amide LC-MS: $t_R$=1.11 min; [M+H]$^+$=571.12.

Example 27

(S)-1-methyl-1H-indole-3-carboxylic acid{1-[5-(2-fluoro-phenyl)-2-(3-methoxy-phenyl)-thiazole-4-carbonyl]-piperidin-2-ylmethyl}-amide LC-MS: $t_R$=1.11 min; [M+H]$^+$=583.14.

Example 28

(S)-1-methyl-1H-indole-3-carboxylic acid{1-[5-(2-fluoro-phenyl)-2-p-tolyl-thiazole-4-carbonyl]-piperidin-2-ylmethyl}-amide LC-MS: $t_R$=1.14 min; [M+H]$^+$=567.07.

Example 29

(S)-1-methyl-1H-indole-3-carboxylic acid{1-[5-(2-fluoro-phenyl)-2-(4-fluoro-phenyl)-thiazole-4-carbonyl]-piperidin-2-ylmethyl}-amide LC-MS: $t_R$=1.11 min; [M+H]$^+$=571.04.

Example 30

(S)-1-methyl-1H-indole-3-carboxylic acid{1-[5-(2-fluoro-phenyl)-2-(4-methoxy-phenyl)-thiazole-4-carbonyl]-piperidin-2-ylmethyl}-amide LC-MS: $t_R$=1.11 min; [M+H]$^+$=583.11.

Example 31

(S)-2,3-dihydro-benzofuran-4-carboxylic acid{1-[2-phenyl-5-(3-trifluoromethyl-phenyl)-thiazole-4-carbonyl]-piperidin-2-ylmethyl}-amide 31.1. (S)-{1-[2-bromo-5-(3-trifluoromethyl-phenyl)-thiazole-4-carbonyl]-piperidin-2-ylmethyl}-carbamic acid tent-butyl ester:

This compound was prepared using a method analogous to that of Example 1, step 1.1. LC-MS: $t_R$=1.08 min; [M+H]$^+$=548.06.

31.2. (S)-(2-aminomethyl-piperidin-1-yl)42-bromo-5-(3-trifluoromethyl-phenyl)-thiazol-4-yl]-methanone:

This compound was prepared from intermediate 31.1 using a method analogous to that of Example 17, step 17.2. LC-MS: $t_R$=0.80 min; [M+H]$^-$=448.04.

31.3. (S)-2,3-dihydro-benzofuran-4-carboxylic acid{1-[2-bromo-5-(3-trifluoromethyl-phenyl)-thiazole-4-carbonyl]-piperidin-2-ylmethyl}-amide:

This compound was prepared from intermediate 31.2 using a method analogous to that of Example 1, step 1.3. LC-MS: $t_R$=1.10 min; [M+H]$^+$=594.06.

31.4. (S)-2,3-dihydro-benzofuran-4-carboxylic acid{1-[2-phenyl-5-(3-trifluoromethyl-phenyl)-thiazole-4-carbonyl]-piperidin-2-ylmethyl}-amide This compound was prepared from intermediate 31.3 using a method analogous to that of Example 1, step 1.4. LC-MS: $t_R$=1.15 min; [M+H]$^+$=592.15.

Examples 32 to 38 were prepared according to the sequence described for the preparation of the compound of Example 31, using however different aryl boronic acids in the 4$^{th}$ step.

Example 32

(S)-2,3-dihydro-benzofuran-4-carboxylic acid{1-[2-m-tolyl-5-(3-trifluoromethyl-phenyl)-thiazole-4-carbonyl]-piperidin-2-ylmethyl}-amide LC-MS: $t_R$=1.18 min; [M+H]$^+$=606.15.

Example 33

(S)-2,3-dihydro-benzofuran-4-carboxylic acid{1-[2-(3-fluoro-phenyl)-5-(3-trifluoromethyl-phenyl)-thiazole-4-carbonyl]-piperidin-2-ylmethyl}-amide LC-MS: $t_R$=1.15 min; $[M+H]^+$=610.14.

Example 34

(S)-2,3-dihydro-benzofuran-4-carboxylic acid{1-[2-(3-methoxy-phenyl)-5-(3-trifluoromethyl-phenyl)-thiazole-4-carbonyl]-piperidin-2-ylmethyl}-amide LC-MS: $t_R$=1.15 min; $[M+H]^+$=622.07.

Example 35

(S)-2,3-dihydro-benzofuran-4-carboxylic acid{1-[2-p-tolyl-5-(3-trifluoromethyl-phenyl)-thiazole-4-carbonyl]-piperidin-2-ylmethyl}-amide LC-MS: $t_R$=1.18 min; $[M+H]^+$=606.05.

Example 36

(S)-2,3-dihydro-benzofuran-4-carboxylic acid{1-[2-(4-fluoro-phenyl)-5-(3-trifluoromethyl-phenyl)-thiazole-4-carbonyl]-piperidin-2-ylmethyl}-amide LC-MS: $t_R$=1.15 min; $[M+H]^+$=610.18.

Example 37

(S)-2,3-dihydro-benzofuran-4-carboxylic acid{1-[2-(4-methoxy-phenyl)-5-(3-trifluoromethyl-phenyl)-thiazole-4-carbonyl]-piperidin-2-ylmethyl}-amide LC-MS: $t_R$=1.16 min; $[M+H]^+$=622.08.

Example 38

(S)-6-methyl-imidazo[2,1-b]thiazole-5-carboxylic acid[1-(2-phenyl-5-p-tolyl-thiazole-4-carbonyl)-piperidin-2-ylmethyl]-amide LC-MS: $t_R$=0.89 min; $[M+H]^+$=556.39.

Example 39

(S)-2,3-dihydro-benzofuran-4-carboxylic acid{1-[5-(3-chloro-phenyl)-2-pyridin-4-yl-thiazole-4-carbonyl]-pyrrolidin-2-ylmethyl}-amide

39.1. (S)-2-[(2,2,2-trifluoro-acetylamino)-methyl]-pyrrolidine-1-carboxylic acid tert-butyl ester:

(S)-2-aminomethyl-pyrrolidine-1-carboxylic acid tert-butyl ester (10 g, 49.93 mmol) was dissolved in THF (200 ml) followed by the dropwise addition, within 5 min, of ethyl trifluoroacetate (9.75 g, 67.95 mmol) dissolved in THF (50 ml). Stirring was continued for 3 h at RT. The reaction mixture was concentrated under reduced pressure and the residue dried at HV to give the expected compound (14.86 g). LC-MS: $t_R$=0.93 min; $[M+H]^-$=297.29.

39.2. (S)-2,2,2-trifluoro-N-pyrrolidin-2-ylmethyl-acetamide hydrochloride:

Intermediate 39.1 (13.87 g, 46.81 mmol) was dissolved in THF (200 ml), followed by the addition of HCl in dioxane (4M, 70 ml) within 5 min. Stirring was continued for 2 h at RT. The reaction mixture was concentrated in vacuo. The residue was taken up into ether (100 ml) and the precipitated powder was filtered off to give the expected compound (11.2 g). LC-MS: $t_R$=0.25 min; $[M+H]^+$=197.29.

39.3. (S)-N-{1-[5-(3-chloro-phenyl)-2-pyridin-4-yl-thiazole-4-carbonyl]-pyrrolidin-2-ylmethyl}-2,2,2-trifluoro-acetamide:

5-(3-chloro-phenyl)-2-pyridin-4-yl-thiazole-4-carboxylic acid (215 mg, 0.68 mmol) was dissolved in acetonitrile (10 ml), followed by the addition of TBTU (240 mg, 0.74 mmol) and DIPEA (0.582 ml, 3.39 mmol). Stirring at RT was continued for 10 min, followed by the addition of intermediate 39.2 (158 mg, 0.68 mmol) and DMF (2.5 ml). Stirring at RT was continued for 20 h. The mixture was concentrated under reduced pressure. Water (25 ml) and aq. HCl (1M) was added until pH=1. The aq. phase was extracted with EtOAc (2×25 ml). The combined org. layers were washed with aq. NaOH solution (1M, 25 ml) and brine (25 ml), dried over magnesium sulfate, filtered and the solvent was evaporated under reduced pressure. The residue was purified by flash chromatography (SiO$_2$, DCM/MeOH=98/2) to give the expected compound (228 mg). LC-MS: $t_R$=0.91 min; $[M+H]^+$=494.87.

39.4. (S)-(2-aminomethyl-pyrrolidin-1-yl)-[5-(3-chloro-phenyl)-2-pyridin-4-yl-thiazol-4-yl]-methanone:

Intermediate 39.3 (224 mg, 0.452 mmol) was dissolved in MeOH (1.6 ml) followed by the addition of an aq. sat. solution of K$_2$CO$_3$ (1.1 ml). Stirring was continued at 60° C. for 3 h. The MeOH was distilled off under reduced pressure. Na$_2$SO$_4$ (2 g) was added to the aq. residue followed by DCM. The suspension was stirred for 1 h and the Na$_2$SO$_4$ was filtered off, washed with DCM and the DCM was removed under reduced pressure. The residue was dried at HV to give the expected compound (153 mg). LC-MS: $t_R$=0.72 min; $[M+H]^+$=398.97.

39.5. (S)-2,3-dihydro-benzofuran-4-carboxylic acid{1-[5-(3-chloro-phenyl)-2-pyridin-4-yl-thiazole-4-carbonyl]-pyrrolidin-2-ylmethyl}-amide:

2,3-dihydro-benzofuran-4-carboxylic acid (21 mg, 0.125 mmol) was dissolved in acetonitrile (1 ml) followed by the addition of TBTU (44 mg, 0.138 mmol) and DIPEA (81 mg, 0.627 mmol). The reaction mixture was stirred for 15 min at RT. Intermediate 39.4 (50 mg, 0.125 mmol), dissolved in acetonitrile (0.5 ml) was added and stirring continued for 20 h at RT. The reaction mixture was purified by prep. HPLC to give the expected compound (11 mg). LC-MS: $t_R$=0.84-0.94 min; $[M+H]^+$=544.07.

The compounds of Examples 40 and 41 were prepared according to the procedure described for Example 39, 2,3-dihydro-benzofuran-4-carboxylic acid being replaced by the appropriate acid in the last step.

Example 40

(S)-6-methyl-imidazo[2,1-b]thiazole-5-carboxylic acid{1-[5-(3-chloro-phenyl)-2-pyridin-4-yl-thiazole-4-carbonyl]-pyrrolidin-2-ylmethyl}-amide LC-MS: $t_R$=0.78-0.84 min; [M+H]$^+$=562.88.

Example 41

(S)-1-methyl-1H-indazole-3-carboxylic acid{1-[5-(3-chloro-phenyl)-2-pyridin-4-yl-thiazole-4-carbonyl]-pyrrolidin-2-ylmethyl}-amide LC-MS: $t_R$=0.84-0.92 min; [M+H]$^+$=556.93.

Example 42

(S)-6-methyl-imidazo[2,1-b]thiazole-5-carboxylic acid{1-[5-(3-chloro-phenyl)-2-pyridin-3-yl-thiazole-4-carbonyl]-pyrrolidin-2-ylmethyl}-amide 42.1. (5)-N-{1-[5-(3-chloro-phenyl)-2-pyridin-3-yl-thiazole-4-carbonyl]-pyrrolidin-2-ylmethyl}-2,2,2-trifluoro-acetamide:

5-(3-chloro-phenyl)-2-pyridin-3-yl-thiazole-4-carboxylic acid (219 mg, 0.69 mmol) was dissolved in acetonitrile (10 ml), followed by the addition of TBTU (245 mg, 0.76 mmol) and DIPEA (0.593 ml, 3.46 mmol). Stirring at RT was continued for 10 min, followed by the addition of intermediate 39.2 (161 mg, 0.69 mmol) and DMF (2.5 ml). Stirring at RT was continued for 20 h. The mixture was concentrated under reduced pressure. Water (25 ml) and aq. HCl (1 M) was added until pH=1. The aq. phase was extracted with EtOAc (2×25 ml). The combined org. layers were washed with aq. NaOH solution (1M, 25 ml) and brine (25 ml), dried over MgSO$_4$ and filtered. The solvent was evaporated under reduced pressure and the residue was purified by flash chromatography (SiO$_2$, DCM/MeOH=99/1) to give the expected compound (206 mg). LC-MS: $t_R$=1.04 min; [M+H]$^-$=495.20.

42.2. (S)-(2-aminomethyl-pyrrolidin-1-yl)-[5-(3-chloro-phenyl)-2-pyridin-3-yl-thiazol-4-yl]-methanone:

Intermediate 42.1 (203 mg, 0.411 mmol) was dissolved in MeOH (1.6 ml) followed by the addition of an aq. sat. solution of K$_2$CO$_3$ (1.1 ml). Stirring was continued at 60° C. for 3 h. The MeOH was distilled off under reduced pressure. Na$_2$SO$_4$ (2 g) was added to the aq. residue followed by DCM. The suspension was stirred for 1 h and the Na$_2$SO$_4$ was filtered off, washed with DCM and the DCM was removed under reduced pressure. The residue was dried at HV to give the expected compound (152 mg). LC-MS: $t_R$=0.78 min; [M+H]$^-$=398.97.

42.3. (S)-6-methyl-imidazo[2,1-b]thiazole-5-carboxylic acid{1-[5-(3-chloro-phenyl)-2-pyridin-3-yl-thiazole-4-carbonyl]-pyrrolidin-2-ylmethyl}-amide:

6-methyl-imidazo[2,1-b]thiazole-5-carboxylic acid (23 mg, 0.125 mmol) was dissolved in acetonitrile (1 ml) followed by the addition of TBTU (44 mg, 0.138 mmol) and DIPEA (81 mg, 0.627 mmol). The reaction mixture was stirred for 15 min at rt. Intermediate 42.2 (50 mg, 0.125 mmol), dissolved in acetonitrile (0.5 ml), was added and stirring continued for 20 h at RT. The reaction mixture was purified by prep. HPLC to give the expected compound (39 mg). LC-MS: $t_R$=0.82-0.92 min; [M+H]$^+$=562.89.

The compounds of Examples 43 to 52 were prepared according to a procedure similar to the procedure described for Example 42.

Example 43

(S)-benzofuran-4-carboxylic acid{1-[5-(3-chloro-phenyl)-2-pyridin-3-yl-thiazole-4-carbonyl]-pyrrolidin-2-ylmethyl}-amide LC-MS: $t_R$=0.89-1.07 min; [M+H]$^+$=542.83

Example 44

(S)-1-methyl-1H-indazole-3-carboxylic acid{1-[5-(3-chloro-phenyl)-2-pyridin-3-yl-thiazole-4-carbonyl]-pyrrolidin-2-ylmethyl}-amide LC-MS: $t_R$=0.90-1.01 min; [M+H]$^+$=556.93.

Example 45

(S)-6-methyl-imidazo[2,1-b]thiazole-5-carboxylic acid{1-[5-(4-fluoro-phenyl)-2-m-tolyl-thiazole-4-carbonyl]-pyrrolidin-2-ylmethyl}-amide LC-MS: $t_R$=0.95 min; [M+H]$^+$=560.19.

Example 46

(S)-6-methyl-imidazo[2,1-b]thiazole-5-carboxylic acid{1-[5-(4-fluoro-phenyl)-2-p-tolyl-thiazole-4-carbonyl]-pyrrolidin-2-ylmethyl}-amide LC-MS: $t_R$=0.95 min; [M+H]$^+$=560.19.

Example 47

(S)-6-methyl-imidazo[2,1-b]thiazole-5-carboxylic acid{1-[5-(4-fluoro-phenyl)-2-(2-fluoro-phenyl)-thiazole-4-carbonyl]-pyrrolidin-2-ylmethyl}-amide LC-MS: $t_R$=0.93 min; [M+H]$^+$=564.18.

Example 48

(S)-6-methyl-imidazo[2,1-b]thiazole-5-carboxylic acid{1-[5-(4-fluoro-phenyl)-2-(3-fluoro-phenyl)-thiazole-4-carbonyl]-pyrrolidin-2-ylmethyl}-amide LC-MS: $t_R$=0.93 min; [M+H]$^+$=564.19.

Example 49

(S)-6-methyl-imidazo[2,1-b]thiazole-5-carboxylic acid{1-[2,5-bis-(4-fluoro-phenyl)-thiazole-4-carbonyl]-pyrrolidin-2-ylmethyl}-amide LC-MS: $t_R$=0.92 min; [M+H]$^+$=564.18.

Example 50

(S)-6-methyl-imidazo[2,1-b]thiazole-5-carboxylic acid{1-[5-(4-fluoro-phenyl)-2-(2-methoxy-phenyl)-thiazole-4-carbonyl]-pyrrolidin-2-ylmethyl}-amide LC-MS: $t_R$=0.89 min; [M+H]$^+$=576.24.

Example 51

(S)-6-methyl-imidazo[2,1-b]thiazole-5-carboxylic acid{1-[5-(4-fluoro-phenyl)-2-(3-methoxy-phenyl)-thiazole-4-carbonyl]-pyrrolidin-2-ylmethyl}-amide LC-MS: $t_R$=0.89 min; [M+H]$^+$=576.23.

Example 52

(S)-6-methyl-imidazo[2,1-b]thiazole-5-carboxylic acid{1-[5-(4-fluoro-phenyl)-2-(4-methoxy-phenyl)-thiazole-4-carbonyl]-pyrrolidin-2-ylmethyl}-amide- LC-MS: $t_R$=0.89 min; [M+H]$^+$=576.24.

Biological Assays

In Vitro Assay

The orexin receptor antagonistic activity of the compounds of formula (I) is determined in accordance with one of the following experimental methods.

Experimental Method:

Chinese hamster ovary (CHO) cells expressing the human orexin-1 receptor and the human orexin-2 receptor, respectively, are grown in culture medium (Ham F-12 with L-Glutamine) containing 300 μg/ml G418, 100 U/ml penicillin, 100 μg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH: water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates, first in DMSO, then in HBSS containing 0.1% bovine serum albumin (BSA), $NaHCO_3$: 0.375 g/l and 20 mM HEPES.

On the day of the assay, 50 μl of staining buffer (HBSS containing 1% FCS, 20 mM HEPES, $NaHCO_3$: 0.375 g/l, 5 mM probenecid (Sigma) and 3 μM of the fluorescent calcium indicator fluo-4 AM (1 mM stock solution in DMSO, containing 10% pluronic) is added to each well.

The 384-well cell-plates are incubated for 50 min at 37° C. in 5% $CO_2$ followed by equilibration at RT for 30-120 min before measurement.

Within the Fluorescent Imaging Plate Reader (FLIPR2 or FLIPR Tetra, Molecular Devices), antagonists are added to the plate in a volume of 10 μl/well, incubated for 10 min and finally 10 μl/well of agonist is added. Fluorescence is measured for each well at 1 second intervals, and the height of each fluorescence peak is compared to the height of the fluorescence peak induced by 3 nM orexin-A with vehicle in place of antagonist. For each antagonist, the $IC_{50}$ value (the concentration of compound needed to inhibit 50% of the agonistic response) is determined. Optimized conditions may be achieved by adjustment of pipetting speed and cell splitting regime. The calculated $IC_{50}$ values of the compounds may fluctuate depending on the daily cellular assay performance. Fluctuations of this kind are known to those skilled in the art.

Antagonistic activities ($IC_{50}$ values) of all exemplified compounds are below 1000 nM with respect to the OX1 and/or the OX2 receptor. $IC_{50}$ values of all exemplified compounds are in the range of 1-414 nM with respect to the OX1 receptor. $IC_{50}$ values of 50 exemplified compounds are in the range of 7-5330 nM with respect to the OX2 receptor; 2 compounds have been measured with an $IC_{50}$ value >10000 nM in this assay. Antagonistic activities of selected compounds are displayed in Table 1.

TABLE 1

| Compound of Example | $OX_1$ $IC_{50}$ (nM) | $OX_2$ $IC_{50}$ (nM) |
|---|---|---|
| 3 | 1 | 24 |
| 5 | 2 | 7 |
| 17 | 20* | 68* |
| 24 | 10* | 60* |
| 38 | 2 | 8 |
| 44 | 9* | 18* |
| 45 | 1 | 12 |

$IC_{50}$ values measured with FLIPR 2 or, if marked with *, with FLIPR Tetra;

The invention claimed is:

1. A compound of formula I

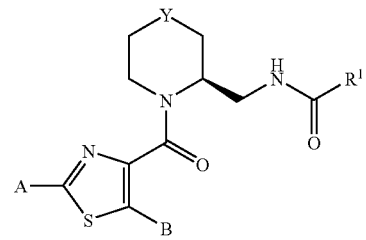

wherein

Y represents $(CH_2)_n$, wherein n represents 1;

A represents pyridyl, unsubstituted phenyl or phenyl mono- or di-substituted with substituents independently selected from the group consisting of $(C_{1-4})$alkyl, $(C_{1-4})$alkoxy, trifluoromethyl and halogen;

B represents phenyl which is unsubstituted or mono- or di-substituted with substituents independently selected from the group consisting of $(C_{1-4})$alkyl, $(C_{1-4})$alkoxy, trifluoromethyl and halogen; and $R^1$ represents aryl or heterocyclyl, wherein the aryl or heterocyclyl is unsubstituted or mono-, di-, or tri-substituted with substituents independently selected from the group consisting of $(C_{1-4})$alkyl, $(C_{1-4})$alkoxy, halogen and trifluoromethyl, or $R^1$ represents one of the 2,3-dihydro-benzofuranyl, benzo[1,3]dioxolyl, 2,3-dihydro-benzo[1,4]dioxinyl and 4H-benzo[1,3]dioxinyl groups, which groups are unsubstituted or mono- or di-substituted with substituents independently selected from the group consisting of $(C_{1-4})$alkyl, $(C_{1-4})$alkoxy and halogen;

or a salt of such a compound.

2. The compound of formula I according to claim 1 which is also a compound of formula $I_{CE}$

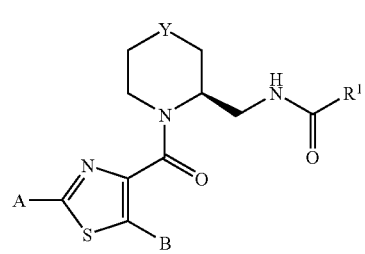

wherein

Y represents $(CH_2)_n$, wherein n represents 1;

A represents pyridyl, unsubstituted phenyl or phenyl which is mono- or di-substituted with substituents independently selected from the group consisting of $(C_{1-4})$alkyl, $(C_{1-4})$alkoxy, trifluoromethyl and halogen;

B represents phenyl which is unsubstituted or substituted once with $(C_{1-4})$alkyl, $(C_{1-4})$alkoxy, trifluoromethyl or halogen; and $R^1$ represents an 8-membered bicyclic aromatic ring containing 1, 2 or 3 heteroatoms independently selected from oxygen, nitrogen and sulphur, which aromatic ring may be substituted once by $(C_{1-4})$alkyl, or $R^1$ represents a 2,3-dihydrobenzofuran-4-yl,1H-indol-3-yl or 1H-indazol-3-yl group which may be substituted once with $(C_{1-4})$alkyl;

or a salt of such a compound.

3. The compound of formula I according to claim 1, wherein $R^1$ represents one of the following groups

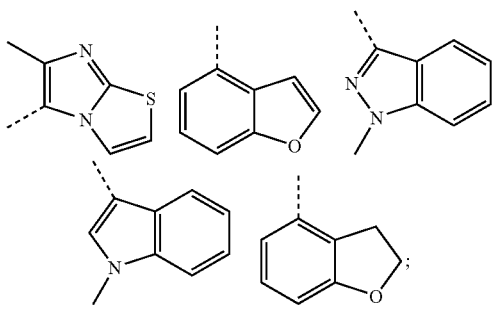

or a salt of such a compound.

4. The compound of formula I according to claim 1, wherein B represents phenyl which is unsubstituted or mono- or di-substituted with substituents independently selected from the group consisting of $(C_{1-4})$alkyl, $(C_{1-4})$alkoxy, trifluoromethyl and halogen;

or a salt of such a compound.

5. The compound of formula I according to claim 1, wherein A represents a pyridyl ring;

or a salt of such a compound.

6. The compound of formula I according to claim 1, wherein A represents phenyl which is unsubstituted or mono-substituted with methyl, fluorine or trifluoromethyl;

or a salt of such a compound.

7. The compound of formula I according to claim 1, wherein:

Y represents $(CH_2)_n$, wherein n represents 1;

B represents phenyl which is mono-substituted with $(C_{1-4})$alkyl, trifluoromethyl or halogen;

A represents 3-pyridyl, 4-pyridyl or a phenyl ring wherein the phenyl ring is unsubstituted or mono-substituted with methyl, fluorine or trifluoromethyl; and $R^1$ is selected from the following groups:

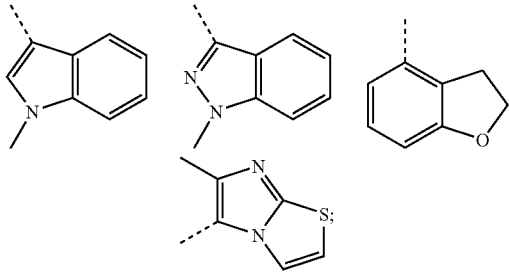

or a salt of such a compound.

8. The compound of formula I according to claim 1, which is selected from the group consisting of:

(S)-6-methyl-imidazo[2,1-b]thiazole-5-carboxylic acid{1-[5-(4-fluoro-phenyl)-2-(2-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(3-fluoro-phenyl)-thiazole-4-carbonyl]-piperidin-2-ylmethyl}-amide;

(S)-6-methyl-imidazo[2,1-b]thiazole-5-carboxylic acid{1-[2,5-bis-(4-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(2-methoxy-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(3-methoxy-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-(4-methoxy-phenyl)-thiazole-4-carbonyl]-piperidin-2-ylmethyl}-amide;

(S)-6-methyl-imidazo[2,1-b]thiazole-5-carboxylic acid{1-[2-(3,5-difluoro-phenyl)-5-(4-fluoro-phenyl)-thiazole-4-carbonyl]-piperidin-2-ylmethyl}-amide;

(S)-6-methyl-imidazo[2,1-b]thiazole-5-carboxylic acid{1-[2-(3,5-difluoro-phenyl)-5-(4-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-m-tolyl-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-p-tolyl-thiazole-4-carbonyl]-piperidin-2-ylmethyl}-amide;

(S)-6-methyl-imidazo[2,1-b]thiazole-5-carboxylic acid{1-[2-(2-fluoro-5-methyl-phenyl)-5-(4-fluoro-phenyl)-thiazole-4-carbonyl]-piperidin-2-ylmethyl}-amide;

(S)-6-methyl-imidazo[2,1-b]thiazole-5-carboxylic acid{1-[2-(3-fluoro-4-methyl-phenyl)-5-(4-fluoro-phenyl)-thiazole-4-carbonyl]-piperidin-2-ylmethyl}-amide;

(S)-6-methyl-imidazo[2,1-b]thiazole-5-carboxylic acid{1-[2-(4-fluoro-2-methyl-phenyl)-5-(4-fluoro-phenyl)-thiazole-4-carbonyl]-piperidin-2-ylmethyl}-amide;

(S)-6-methyl-imidazo[2,1-b]thiazole-5-carboxylic acid{1-[5-(4-fluoro-phenyl)-2-o-tolyl-thiazole-4-carbonyl]-piperidin-2-ylmethyl}-amide;

(S)-2,3-dihydro-benzofuran-4-carboxylic acid{1-[5-(2-fluoro-phenyl)-2-phenyl-thiazole-4-carbonyl]-piperidin-2-ylmethyl}-amide;

(S)-2,3-dihydro-benzofuran-4-carboxylic acid{1-[5-(2-fluoro-phenyl)-2-m-tolyl-thiazole-4-carbonyl]-piperidin-2-ylmethyl}-amide;

(S)-2,3-dihydro-benzofuran-4-carboxylic acid{1-[5-(2-fluoro-phenyl)-2-(3-fluoro-phenyl)-thiazole-4-carbonyl]-piperidin-2-ylmethyl}-amide;

(S)-2,3-dihydro-benzofuran-4-carboxylic acid{1-[5-(2-fluoro-phenyl)-2-(3-methoxy-phenyl)-thiazole-4-carbonyl]-piperidin-2-ylmethyl}-amide;

(S)-2,3-dihydro-benzofuran-4-carboxylic acid{1-[5-(2-fluoro-phenyl)-2-p-tolyl-thiazole-4-carbonyl]-piperidin-2-ylmethyl}-amide;

(S)-2,3-dihydro-benzofuran-4-carboxylic acid{1-[5-(2-fluoro-phenyl)-2-(4-fluoro-phenyl)-thiazole-4-carbonyl]-piperidin-2-ylmethyl}-amide;

- (S)-2,3-dihydro-benzofuran-4-carboxylic acid{1-[5-(2-fluoro-phenyl)-2-(4-methoxy-phenyl)-thiazole-4-carbonyl]-piperidin-2-ylmethyl}-amide;
- (S)-1-methyl-1H-indole-3-carboxylic acid{1-[5-(2-fluoro-phenyl)-2-phenyl-thiazole-4-carbonyl]-piperidin-2-ylmethyl}-amide;
- (S)-1-methyl-1H-indole-3-carboxylic acid{1-[5-(2-fluoro-phenyl)-2-m-tolyl-thiazole-4-carbonyl]-piperidin-2-ylmethyl}-amide;
- (S)-1-methyl-1H-indole-3-carboxylic acid{1-[5-(2-fluoro-phenyl)-2-(3-fluoro-phenyl)-thiazole-4-carbonyl]-piperidin-2-ylmethyl}-amide;
- (S)-1-methyl-1H-indole-3-carboxylic acid{1-[5-(2-fluoro-phenyl)-2-(3-methoxy-phenyl)-thiazole-4-carbonyl]-piperidin-2-ylmethyl}-amide;
- (S)-1-methyl-1H-indole-3-carboxylic acid{1-[5-(2-fluoro-phenyl)-2-p-tolyl-thiazole-4-carbonyl]-piperidin-2-ylmethyl}-amide;
- (S)-1-methyl-1H-indole-3-carboxylic acid{1-[5-(2-fluoro-phenyl)-2-(4-fluoro-phenyl)-thiazole-4-carbonyl]-piperidin-2-ylmethyl}-amide
- (S)-1-methyl-1H-indole-3-carboxylic acid{1-[5-(2-fluoro-phenyl)-2-(4-methoxy-phenyl)-thiazole-4-carbonyl]-piperidin-2-ylmethyl}-amide;
- (S)-2,3-dihydro-benzofuran-4-carboxylic acid{1[2-phenyl-5-(3-trifluoromethyl-phenyl)-thiazole-4-carbonyl]-piperidin-2-ylmethyl}-amide;
- (S)-2,3-dihydro-benzofuran-4-carboxylic acid{1-[2-(3-fluoro-phenyl)-5-(3-trifluoromethyl-phenyl)-thiazole-4-carbonyl]-piperidin-2-ylmethyl}-amide;
- (S)-2,3-dihydro-benzofuran-4-carboxylic acid{1-[2-(3-methoxy-phenyl)-5-(3-trifluoromethyl-phenyl)-thiazole-4-carbonyl]-piperidin-2-ylmethyl}-amide;
- (S)-2,3-dihydro-benzofuran-4-carboxylic acid{1-[2-(4-fluoro-phenyl)-5-(3-trifluoromethyl-phenyl)-thiazole-4-carbonyl]-piperidin-2-ylmethyl}-amide; and
- (S)-6-methyl-imidazo[2,1-b]thiazole-5-carboxylic acid[1-(2-phenyl-5-p-tolyl-thiazole-4-carbonyl)-piperidin-2-ylmethyl]-amide;

or a salt of such a compound.

9. The compound of formula I according to claim 1, or a pharmaceutically acceptable salt of such a compound.

10. A pharmaceutical composition comprising a therapeutically effective amount of a compound of formula I according to claim 1, or a pharmaceutically acceptable salt of such a compound, and at least one pharmaceutically acceptable carrier.

11. A method for the treatment of insomnia in a patient in need thereof comprising administering a pharmaceutically effective amount of a compound according to claim 1, or a pharmaceutically acceptable salt form.

* * * * *